United States Patent
Cholette

(10) Patent No.: US 8,050,760 B2
(45) Date of Patent: Nov. 1, 2011

(54) SYSTEM AND METHOD FOR EVALUATING MECHANICAL CARDIAC DYSSYNCHRONY BASED ON MULTIPLE IMPEDANCE VECTORS USING AN IMPLANTABLE MEDICAL DEVICE

(75) Inventor: Martin Cholette, Acton, CA (US)

(73) Assignee: Pacesetter, Inc., Sylmar, CA (US)

( * ) Notice: Subject to any disclaimer, the term of this patent is extended or adjusted under 35 U.S.C. 154(b) by 399 days.

(21) Appl. No.: 12/270,705

(22) Filed: Nov. 13, 2008

(65) Prior Publication Data

US 2010/0121397 A1   May 13, 2010

(51) Int. Cl.
*A61N 1/00* (2006.01)
*A61B 5/04* (2006.01)

(52) U.S. Cl. ......................................... 607/17; 600/509
(58) Field of Classification Search ................ 607/9, 17, 607/27; 600/509, 515–519
See application file for complete search history.

(56) References Cited

U.S. PATENT DOCUMENTS

| | | | |
|---|---|---|---|
| 5,291,895 A * | 3/1994 | McIntyre | ...................... 600/485 |
| 6,249,705 B1 | 6/2001 | Snell | |
| 6,480,733 B1 | 11/2002 | Turcott | |
| 6,512,952 B2 | 1/2003 | Stahmann et al. | |
| 6,512,953 B2 | 1/2003 | Florio et al. | |
| 6,527,729 B1 | 3/2003 | Turcott | |
| 6,572,557 B2 | 6/2003 | Tchou et al. | |
| 6,628,988 B2 | 9/2003 | Kramer et al. | |
| 6,643,546 B2 | 11/2003 | Mathis et al. | |
| 6,643,548 B1 | 11/2003 | Mai et al. | |
| 6,741,885 B1 | 5/2004 | Park et al. | |
| 6,748,261 B1 | 6/2004 | Kroll et al. | |
| 6,922,587 B2 | 7/2005 | Weinberg | |
| 6,942,622 B1 | 9/2005 | Turcott | |
| 7,010,347 B2 * | 3/2006 | Schecter | ......................... 607/17 |
| 7,072,715 B1 | 7/2006 | Bradley | |
| 2006/0271119 A1 | 11/2006 | Ni et al. | |
| 2006/0271121 A1 | 11/2006 | Ding et al. | |
| 2007/0066905 A1 | 3/2007 | Zhang | |
| 2008/0021504 A1 * | 1/2008 | McCabe et al. | ................... 607/9 |
| 2008/0114410 A1 | 5/2008 | Ding et al. | |
| 2008/0249583 A1 * | 10/2008 | Salo et al. | ....................... 607/11 |
| 2008/0262361 A1 * | 10/2008 | Gutfinger et al. | ............. 600/486 |
| 2008/0306394 A1 * | 12/2008 | Zdeblick et al. | ............. 600/509 |
| 2009/0299211 A1 * | 12/2009 | Wenzel et al. | ................ 600/547 |

* cited by examiner

*Primary Examiner* — Niketa Patel
*Assistant Examiner* — Catherine Voorhees

(57) ABSTRACT

Techniques are provided for evaluating mechanical dyssynchrony within the heart of patient in which a pacemaker, implantable cardioverter-defibrillator (ICD) or other medical device is implanted. In one example, a set of cardiogenic impedance signals are detected along different sensing vectors passing through the heart of the patient, particularly vectors passing through the ventricular myocardium. A measure of mechanical dyssynchrony is detected based on differences, if any, among the cardiogenic impedance signals detected along the different vectors. In particular, differences in peak magnitude delay times, peak velocity delay times, peak magnitudes, and waveform integrals of the cardiogenic impedance signals are quantified and compared to detect abnormally contracting segments, if any, within the heart of the patient. Warnings are generated upon detection of any significant increase in mechanical dyssynchrony. Diagnostic information is recorded for clinical review. Pacing therapies such as cardiac resynchronization therapy (CRT) can be activated or controlled in response to mechanical dyssynchrony to improve the hemodynamic output of the heart.

27 Claims, 12 Drawing Sheets

SYSTEM AND METHOD FOR EVALUATING MECHANICAL CARDIAC DYSSYNCHRONY BASED ON MULTIPLE IMPEDANCE VECTORS USING AN IMPLANTABLE MEDICAL DEVICE

FIELD OF THE INVENTION

The invention generally relates to implantable medical devices, such as pacemakers and implantable cardioverter-defibrillators (ICDs), and in particular to techniques for detecting and evaluating mechanical dyssynchrony within the heart of a patient using such devices, including patients with heart failure.

BACKGROUND OF THE INVENTION

Heart failure is a debilitating disease in which abnormal function of the heart leads in the direction of inadequate blood flow to fulfill the needs of the tissues and organs of the body. Typically, the heart loses propulsive power because the cardiac muscle loses capacity to stretch and contract. Often, the ventricles do not adequately eject or fill with blood between heartbeats and the valves regulating blood flow become leaky, allowing regurgitation or back-flow of blood. The impairment of arterial circulation deprives vital organs of oxygen and nutrients. Fatigue, weakness and the inability to carry out daily tasks may result. Not all heart failure patients suffer debilitating symptoms immediately. Some may live actively for years. Yet, with few exceptions, the disease is relentlessly progressive.

As heart failure progresses, it tends to become increasingly difficult to manage. Even the compensatory responses it triggers in the body may themselves eventually complicate the clinical prognosis. For example, when the heart attempts to compensate for reduced cardiac output, it adds muscle causing the ventricles (particularly the left ventricle) to grow in thickness in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output. A particularly severe form of heart failure is congestive heart failure (CHF) wherein the weak pumping of the heart leads to build-up of fluids in the lungs and other organs and tissues.

Heart failure is often associated with electrical signal conduction defects within the heart. The natural electrical activation system through the heart involves sequential events starting with the sino-atrial (SA) node, and continuing through the atrial conduction pathways of Bachmann's bundle and internodal tracts at the atrial level, followed by the atrio-ventricular (AV) node, the Bundle of His, the right and left bundle branches, with final distribution to the distal myocardial terminals via the Purkinje fiber network. Any of these conduction pathways may potentially be degraded.

A common conduction defect arising in connection with CHF is left bundle branch block (LBBB). The left bundle branch forms a broad sheet of conduction fibers along the septal endocardium of the left ventricle and separates into two or three indistinct fascicles. These extend toward the left ventricular apex and innervate both papillary muscle groups. The main bundle branches are nourished by septal perforating arteries. In a healthy heart, electrical signals are conducted more or less simultaneously through the left and right bundles to trigger synchronous contraction of both the septal and postero-lateral walls of the left ventricle. LBBB occurs when conduction of electrical signals through the left bundle branch is delayed or totally blocked, thereby delaying delivery of the electrical signal to the left ventricle and altering the sequence of activation of that ventricle. The impulse starts in the right ventricle (RV) and crosses the septum causing the interventricular septum to depolarize and hence, contract, first. The electrical impulse continues to be conducted to the postero-lateral wall of the left ventricle causing its activation and depolarization but, due to an inability to use the native conduction system, this activation and contraction is delayed. As such, the posterolateral wall of the left ventricle (LV) only starts to contract after the interventricular septum has completed its contraction and is starting to relax. LBBB thus results in an abnormal activation of the left ventricle inducing desynchronized ventricular contraction (i.e. ventricular dyssynchrony) and impairment in cardiac hemodynamic performance.

Degeneration of the electrical conduction system as manifested by LBBB or other conduction defects may arise due to an acute myocardial infarction but is usually associated with degeneration as a result of chronic ischemia, left ventricular hypertension, general aging and calcification changes, especially any form of cardiac myopathy that results in overt CHF. Present treatments are directed towards correcting this electrical correlate by pacing on the left side of the heart and/or pacing on both sides of the left ventricle (lateral-posterior wall and septum) to improve contractile coordination. One particular technique for addressing LBBB is cardiac resynchronization therapy (CRT), which seeks to normalize asynchronous cardiac electrical activation by delivering synchronized pacing stimulus to both sides of the ventricles using pacemakers or ICDs equipped with biventricular pacing capability, i.e. CRT seeks to reduce or eliminate ventricular dyssynchrony.

Ventricular stimulus is synchronized so as to help to improve overall cardiac function. This may have the additional beneficial effect of reducing the susceptibility to life-threatening tachyarrhythmias. With CRT, pacing pulses are delivered directly to the left ventricle in an attempt to ensure that the left ventricular myocardium will contract more uniformly. CRT may also be employed for patients whose nerve conduction pathways are corrupted due to right bundle branch block (RBBB) or due to other problems such as the development of scar tissue within the myocardium following a myocardial infarction. CRT and related therapies are discussed in, for example, U.S. Pat. No. 6,643,546 to Mathis, et al., entitled "Multi-Electrode Apparatus and Method for Treatment of Congestive Heart Failure"; U.S. Pat. No. 6,628,988 to Kramer, et al., entitled "Apparatus and Method for Reversal of Myocardial Remodeling with Electrical Stimulation"; and U.S. Pat. No. 6,512,952 to Stahmann, et al., entitled "Method and Apparatus for Maintaining Synchronized Pacing".

With conventional CRT, an external Doppler-echocardiography system may be used to noninvasively assess cardiac function. It can also be used to assess the effectiveness of any programming changes on overall cardiac function. Then, biventricular pacing control parameters of the pacemaker or ICD are adjusted by a physician using an external programmer in an attempt to synchronize the ventricles and to optimize patient cardiac function. For example, the physician may adjust the interventricular pacing delay, which specifies the time delay between pacing pulses delivered to the right and left ventricles, in an attempt to maximize cardiac output. To assess the effectiveness of any programming change, Doppler-echocardiography, external impedance cardiography or some other independent measure of cardiac function is utilized. However, this evaluation and programming requires an office visit and is therefore a timely and expensive process. Moreover, when relying on any external hemodynamic monitoring system, the control parameters of the pacemaker or ICD cannot be automatically adjusted to respond to on-going changes in patient cardiac function.

Accordingly, it is desirable to configure an implantable device to detect and evaluate the degree of ventricular dyssynchrony within a patient, particularly within those suffering from heart failure, and to automatically adjust the CRT pacing parameters to reduce the degree of dyssynchrony and improve cardiac output. Heretofore, various techniques for use by implantable devices for evaluating dyssynchrony have usually exploited the relative timing of electrical events within an intracardiac electrogram (IEGM) signal sensed by the device to detect electrical dyssynchrony. Exemplary techniques for detecting ventricular electrical dyssynchrony based on IEGM signals and for delivering CRT in response thereto are set forth in some of the above-cited patents. See, also, U.S. Pat. No. 7,676,264, of Pillai et al., filed on Apr. 13, 2007, entitled "Systems and Methods for use by an Implantable Medical Device for Evaluating Ventricular Dyssynchrony based on T-Wave Morphology."

However, the cardiac synchrony that is restored using IEGM-based techniques is principally electrical synchrony. In a diseased myocardium, though, electrical synchrony is not synonymous with mechanical synchrony, the latter of which is responsible for improved hemodynamic output of the heart. Furthermore, left ventricular activation alone is not a unitary process; it is often the case that various segments or portions of the LV can be asynchronous with respect to each other despite otherwise acceptable electrical performance.

Accordingly, it is desirable to provide techniques for detecting and evaluating ventricular mechanical dyssynchrony for use in controlling CRT or other therapies, and it is to this end that the invention is primarily directed.

SUMMARY OF THE INVENTION

In an exemplary embodiment, a method is provided for use with an implantable medical device for detecting and evaluating mechanical cardiac dyssynchrony. Briefly, a set of cardiogenic impedance signals are detected along different sensing vectors within the patient. A measure of mechanical dyssynchrony is detected in the heart of the patient based on a comparison of the set of cardiogenic impedance signals. The measure includes information identifying abnormally contracting segments, if any, within the heart of the patient. Then, at least one function of the implantable device is controlled based on the measure of mechanical dyssynchrony. Such device functions can include, e.g., the recording of diagnostic information pertaining to mechanical dyssynchrony, the generation of warning signals indicating any substantial increase in mechanical dyssynchrony, or the activation or adjustment of CRT or other therapies to improve the hemodynamic output of the heart.

In an illustrative example, the measure of mechanical dyssynchrony is obtained by detecting differences among a set of five cardiogenic impedance signals sensed within the ventricles of a patient using a pacemaker or ICD equipped with multipolar pacing/sensing leads. Any significant differences among the five cardiogenic impedance signals are generally indicative of ventricular mechanical dyssynchrony within the heart. Exemplary differences that are exploited include differences in: (1) peak magnitude delay times of the cardiogenic impedance signals; (2) peak velocity delay times of the cardiogenic impedance signals; (3) peak magnitudes of the cardiogenic impedance signals; and (4) integrals of the cardiogenic impedance signals. Based on these differences, the implantable device detects abnormally contracting segments, if any, including any akinetic segments, hypokinetic segments and/or late contracting segments within the heart of the patient. In addition, the detected differences are used to generate an overall measure of mechanical dyssynchrony to assess global hemodynamics of the heart of the patient. The use of five impedance sensing vectors provides for greater resolution for extrapolating hemodynamic performance than a system exploiting, e.g., only a single impedance sensing vector.

Pacing parameters (such as CRT parameters) are then preferably adjusted so as to decrease the degree of ventricular mechanical dyssynchrony. By adjusting pacing parameters based on mechanical dyssynchrony derived from cardiogenic impedance signals, the pacing parameters can be promptly adjusted to respond to changes within the heart, such as to respond to any deterioration in mechanical synchrony arising due to CHF, conduction defects or other ailments such as myocardial infarction or acute cardiac ischemia. Trends in ventricular mechanical dyssynchrony within the patient may also be identified and tracked to detect, for example, progression of CHF. Appropriate warnings may be generated for the patient, the physician, or both.

System and method implementations are described herein.

BRIEF DESCRIPTION OF THE DRAWINGS

The above and further features, advantages and benefits of the invention will be apparent upon consideration of the descriptions herein taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators are used to refer to like parts or elements throughout.

Overview of Implantable Medical System

Figure 1:
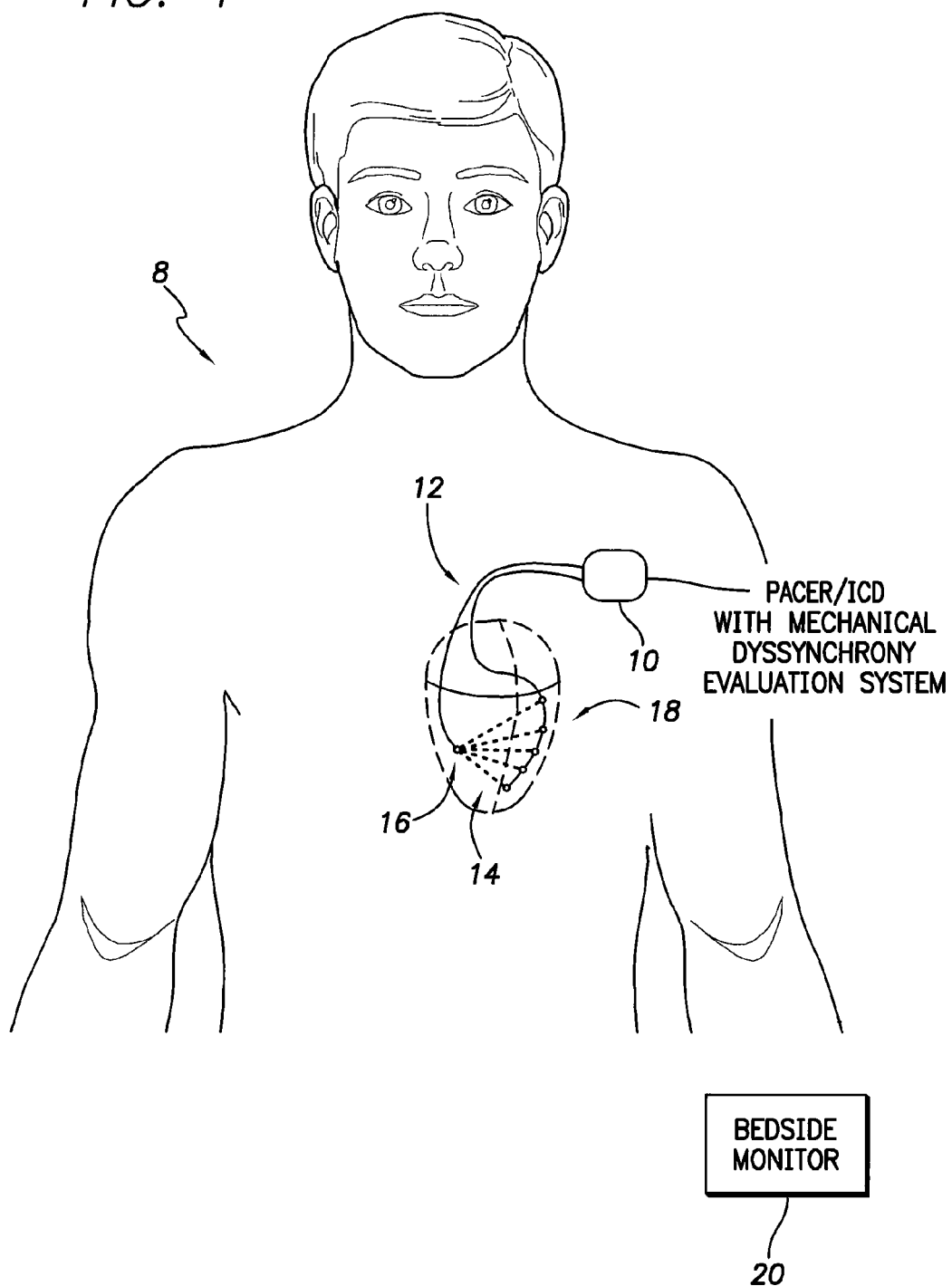
FIG. 1 illustrates pertinent components of an implantable medical system having a pacer/ICD equipped with a mechanical dyssynchrony evaluation system.
Figure 11:
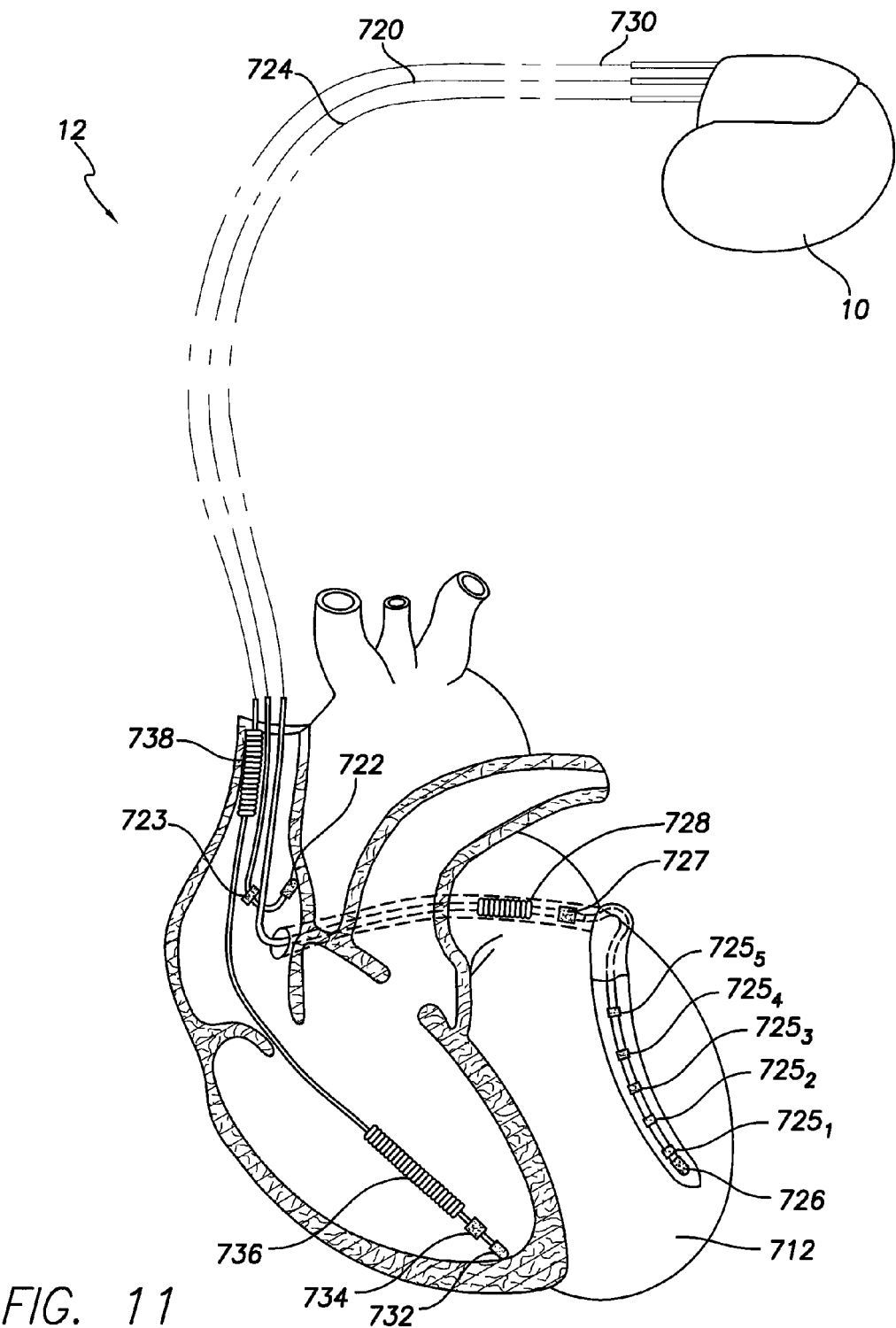
FIG. 11 is a simplified, partly cutaway view, illustrating the pacer/ICD of FIG. 1 along with a more complete set of exemplary leads implanted in the heart of a patient.

FIG. 1 illustrates an implantable medical system 8 capable of detecting and evaluating mechanical dyssynchrony within the heart of a patient based on cardiogenic impedance and also capable of controlling delivery of appropriate therapy in response thereto. To this end, a pacer/ICD 10 (or other implantable medical device) uses one or more multipolar cardiac pacing/sensing leads 12 to detect a set of cardiogenic impedance signals for comparison to one another. The cardiogenic impedance signals are detected along different detection vectors representative of different segments of the heart. In the example of FIG. 1, the cardiogenic impedance signals are detected along a set of sensing vectors 14 between a single RV electrode 16 and a set of separate LV electrodes 18. This is just one exemplary configuration. A more complete set of leads and electrodes is illustrated in FIG. 11, which is described in detail below.

The pacer/ICD analyzes the cardiogenic impedance signals obtained along the different vectors to detect and measure various morphological parameters, such as the peak magnitude, peak velocity, waveform integral, etc. Based on the differences (if any) in the parameters derived from the set of cardiogenic impedance signals, the pacer/ICD detects and quantifies ventricular mechanical synchrony within the patient, evaluates its severity, detects abnormally contracting segments, if any, within the heart of the patient, records diagnostic information and issues warnings, if warranted.

For example, if the degree of ventricular mechanical dyssynchrony within the patient is found to exceed an acceptable threshold, warning signals are generated to warn the patient using either an internal warning device (which is part of the pacer/ICD) or an external bedside monitor 20. The internal warning device may be a vibrating device or a "tickle" voltage device that, in either case, provides perceptible stimulation to the patient to alert the patient so the patient may then consult a physician. If a bedside monitor is provided, the bedside monitor provides audible or visual alarm signals to alert the patient as well as textual or graphic displays. In addition, diagnostic information pertaining to ventricular mechanical dyssynchrony is transferred to the bedside monitor or is stored within the pacer/ICD for subsequent transmission to an external programmer (not shown in FIG. 1) for review by a physician or other medical professional.

External programmers are typically used only during follow-up sessions with the patient wherein a clinician downloads information from the implanted device, reviews the information and then adjusts the control parameters of the implanted device, if needed, via the programmer. Bedside monitors typically download information more frequently, such as once per evening, and can be equipped to relay the most pertinent information to the patient's physician via a communication network. In any case, the physician may then prescribe any appropriate therapies to address the mechanical dyssynchrony. The physician may also adjust the operation of the pacer/ICD to activate, deactivate or otherwise control any therapies that are automatically applied. The bedside monitor may be directly networked with a centralized computing system, such as the HouseCall™ system of St. Jude Medical, for immediately notifying the physician of any significant deterioration in ventricular synchrony. Networking techniques for use with implantable medical systems are set forth, for example, in U.S. Pat. No. 6,249,705 to Snell, entitled "Distributed Network System for Use with Implantable Medical Devices."

In addition, the pacer/ICD adjusts pacing parameters so as to reduce or eliminate the amount of ventricular mechanical dyssynchrony. That is, the pacer/ICD performs a form of CRT adapted to resynchronize mechanical contractions. For example, an AV delay and an LV-RV pacing delay may be adjusted so as to reduce the amount of mechanical dyssynchrony. For dual-chamber devices, the AV delay specifies the time delay between a paced or sensed atrial event and a paced ventricular event. For biventricular pacing devices, the LV-RV delay (sometimes also referred to as just the V-V delay) specifies the time delay between a paced or sensed RV event and a paced LV event. (Note that the LV-RV delay may be negative.)

The pacer/ICD also performs various otherwise conventional operations, such as delivering demand based atrial or ventricular pacing, overdrive pacing therapy, or antitachycardia pacing. The pacer/ICD also monitors the heart for atrial or ventricular fibrillation and delivers cardioversion or defibrillation shocks in response thereto.

Hence, FIG. 1 provides an overview of an implantable system capable of detecting mechanical cardiac dyssynchrony based on the comparison of a set of cardiogenic impedance signals, and further capable of controlling pacing therapy in response thereto, delivering any appropriate warning/notification signals, and recording diagnostics. Embodiments may be implemented that do not necessarily perform all of these functions. For example, embodiments may be implemented that provide only for detection of mechanical dyssynchrony and generation of warning signals but not for automatic control of pacing therapy. Some implementations may not employ a bedside monitor. These are just a few exemplary embodiments. No attempt is made herein to describe all possible combinations of components that may be provided in accordance with the general principles of the invention. In addition, note that the particular locations of the implanted components shown in FIG. 1 are merely illustrative and may not necessarily correspond to actual implant locations.

Overview of Ventricular Mechanical Dyssynchrony Evaluation Techniques

Figure 2:
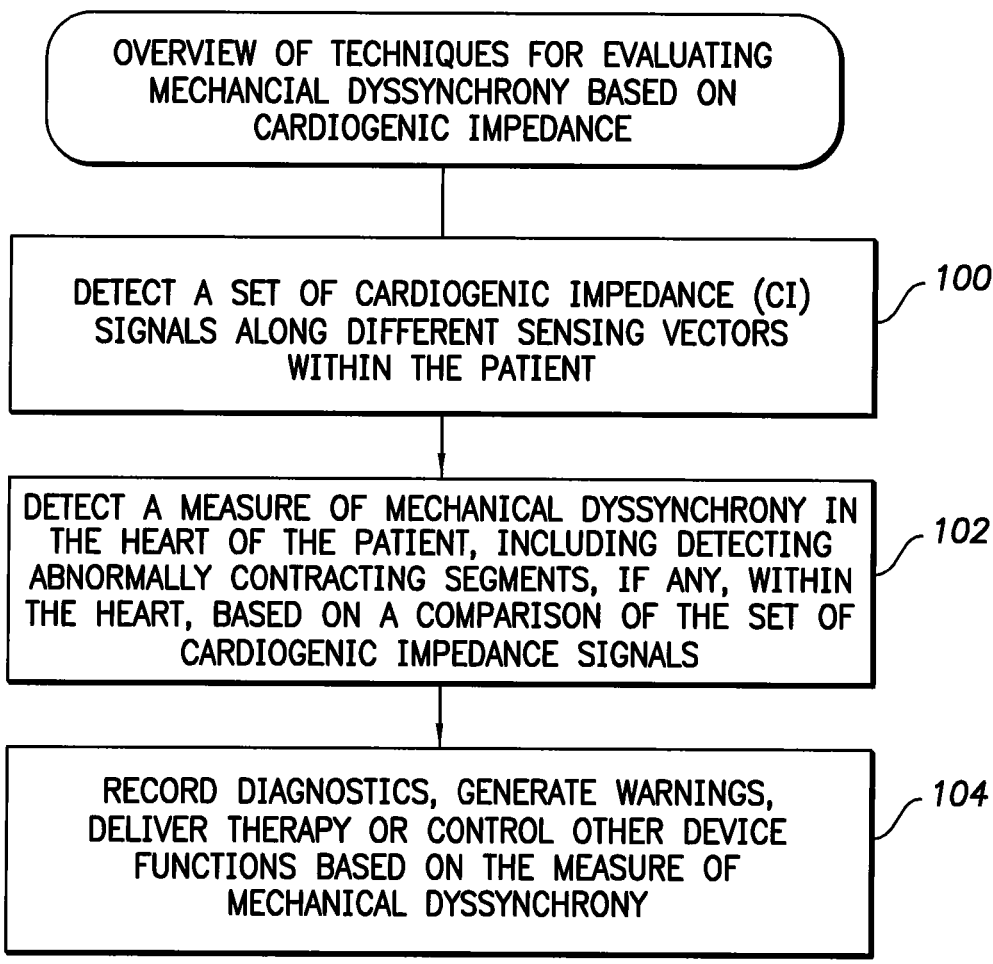
FIG. 2 provides an overview of the method for evaluating mechanical dyssynchrony based on cardiogenic impedance signals performed by the system of FIG. 1.

FIG. 2 broadly summarizes cardiogenic impedance-based techniques of the invention that may be performed by the pacer/ICD of FIG. 1 or by any other suitable device. Briefly, beginning at step 100, the pacer/ICD detects a set of cardiogenic impedance signals along different sensing vectors within the patient, such as by measuring impedance between different pairs of electrodes on the multipolar leads. (Detection of impedance typically involves generating impedance detection pulses from which a raw impedance signal is derived. The raw impedance signal is then processed to derive or extract the cardiogenic portion of the impedance signal, i.e. that portion of the signal affected by the beating of the heart. This is discussed in more detail below.)

At step 102, the pacer/ICD then detects a measure of mechanical dyssynchrony in the heart of the patient based on the cardiogenic impedance signals, including detecting abnormally contracting segments, if any, within the heart of the patient, such as by comparing morphological features of the cardiogenic impedance signals that are affected by increasing mechanical dyssynchrony. Illustrative techniques are described below wherein peak magnitudes, peak time derivatives, and their timing intervals are exploited, alone or in combination. At step 104, the pacer/ICD then record diagnostics, generate warnings, deliver therapy or control other devices functions based on the measure of mechanical dyssynchrony or the detection of abnormally contracting segments. As already explained, the diagnostic data may be transmitted to an external device, such as a bedside monitor or external programmer for subsequent review by a clinician. Warning signals may be generated in response to any significant increase in ventricular mechanical dyssynchrony, which may be indicative of the progression of heart failure or other cardiovascular diseases. Steps 100-104 may be repeated in a loop so as to periodically adjust therapy.

Turning now to the remaining figures, various exemplary systems and techniques for detecting ventricular mechanical dyssynchrony based on cardiogenic impedance signal parameters will now be described in detail.

Illustrative Ventricular Mechanical Dyssynchrony Evaluation Examples

Figure 3:
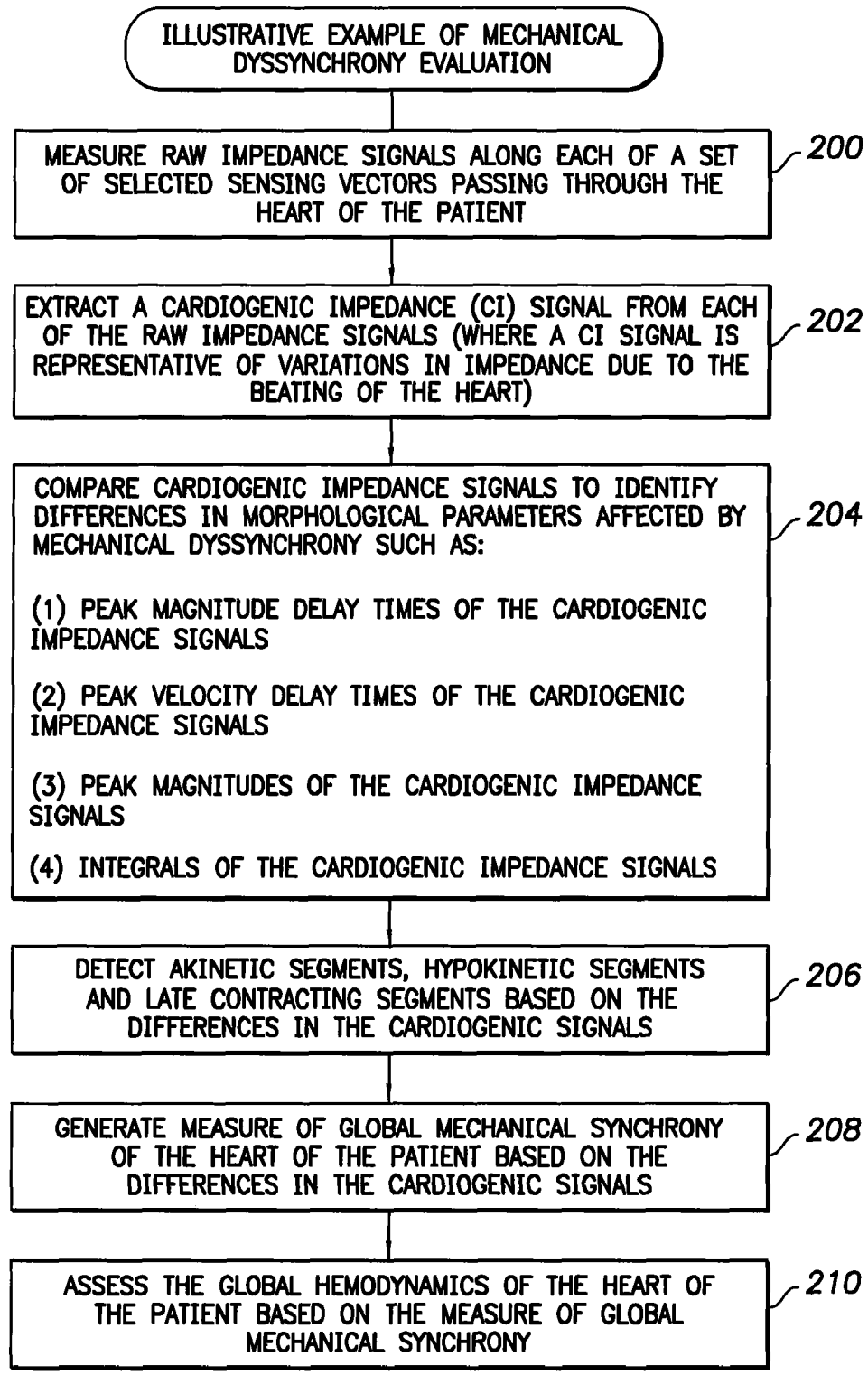
FIG. 3 provides an illustrative example of the general technique of FIG. 2 wherein certain morphological parameters are derived from the cardiogenic impedance signals for use in evaluating ventricular mechanical dyssynchrony.
Figure 4:
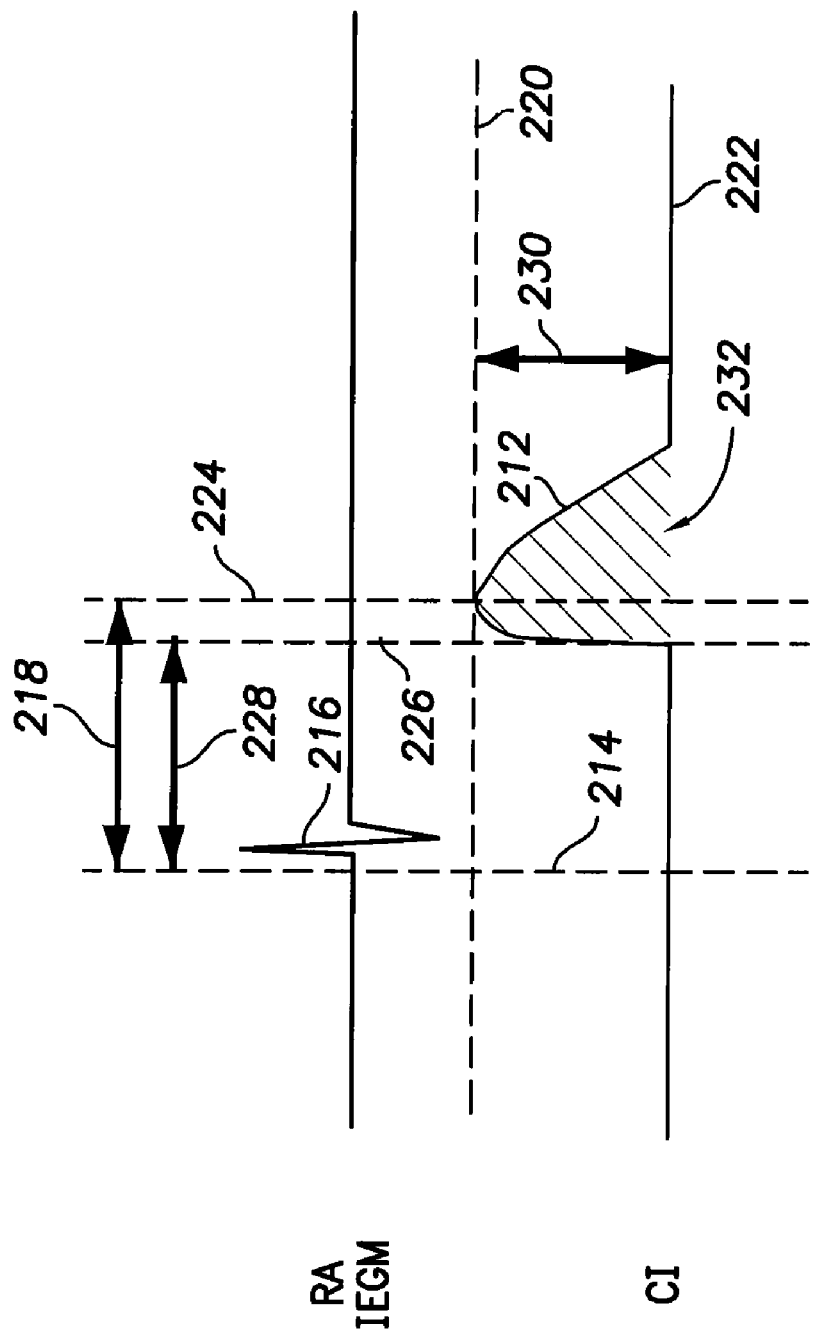
FIG. 4 is a graph illustrating an exemplary cardiogenic impedance signal waveform corresponding to the mechanical contraction of a segment of the heart and, in particular, identifying particular morphological features of the impedance waveform that may be exploited by the technique of FIG. 3 to evaluate mechanical dyssynchrony.
Figure 5:
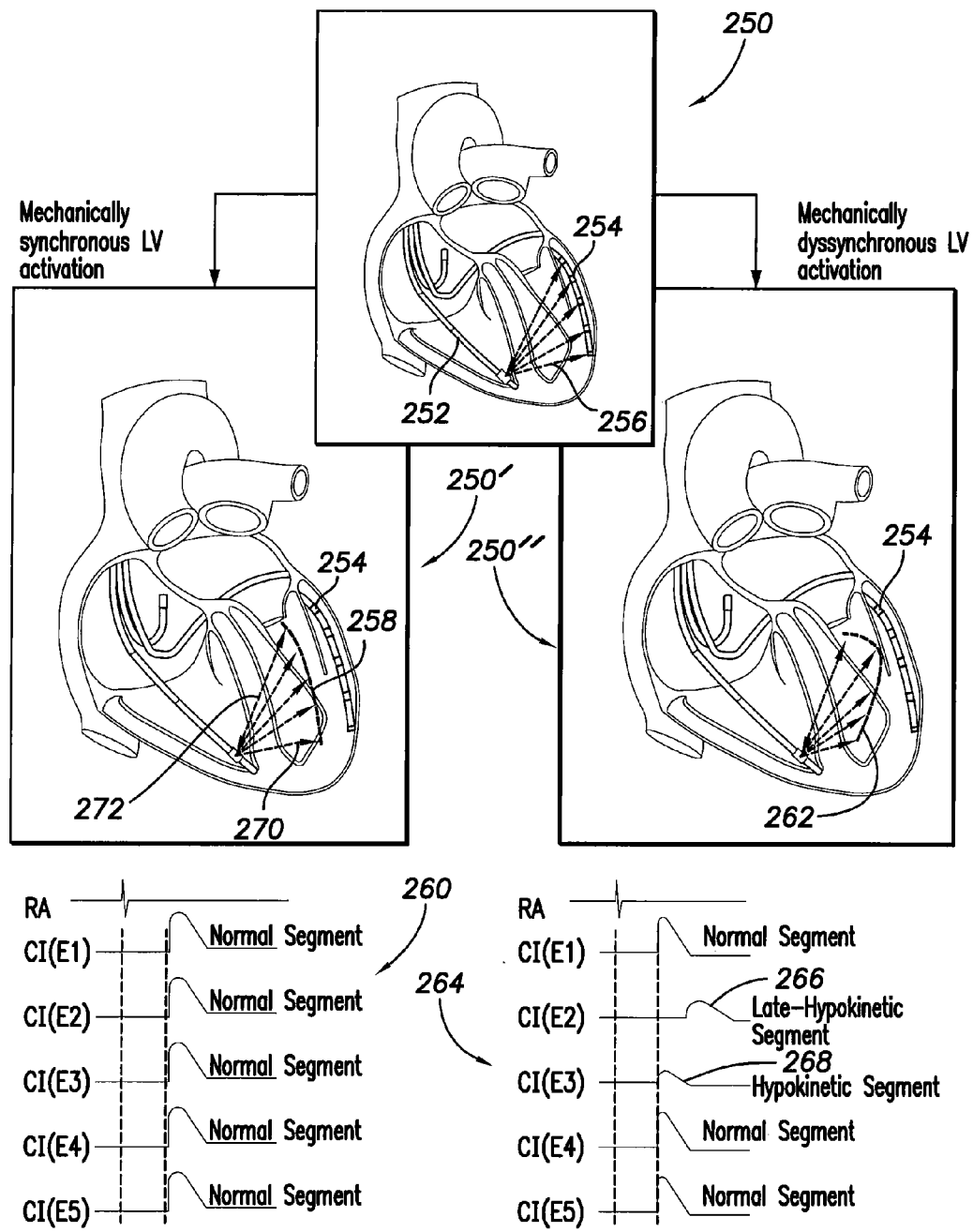
FIG. 5 provides graphical illustrations of the heart of a patient, along with exemplary cardiogenic impedance signal waveforms that may be exploited by the technique of FIG. 3 to detect synchronous and dyssynchronous LV mechanical activation, as well as to identify hypokinetic, akinetic and late contracting LV segments.

FIGS. 3-5 illustrate exemplary techniques for evaluating ventricular mechanical dyssynchrony to detect hypokinetic segments, akinetic segments, late contracting segments of the heart and to assess global heart hemodynamics.

Beginning at step 200 of FIG. 3, the pacer/ICD measures raw impedance signals along each of a set of sensing vectors passing through the heart of the patient and, at step 202, extracts a cardiogenic impedance signal from each of the raw impedance signals (where a "cardiogenic impedance signal" is an signal representative of variations caused by the beating of the heart in impedance or equivalent electrical parameters.)

That is, the device measures a raw impedance signal along each of the selected sensing vectors by applying impedance detection pulses along the vectors, then detecting the resulting impedance signals or values. A particularly effective triphasic impedance detection pulse for use in detecting impedance is described in pending U.S. patent application Ser. No. 11/558,194 of Panescu et al., filed Nov. 9, 2006, entitled "Closed-Loop Adaptive Adjustment of Pacing Therapy based on Cardiogenic Impedance Signals Detected by an Implantable Medical Device." However, other suitable impedance detection pulses or waveforms may instead be exploited. Once the raw impedance signal is detected, the cardiogenic portion of the signal is extracted by, for example, filtering out variations in the raw impedance signal due to patient respiration or other factors. The patent application to Panescu et al. discusses techniques for extracting a cardiogenic impedance signal from a raw signal.

Insofar as the sensing vectors are concerned, each pair of electrodes of the pacing/sensing lead system of the implantable medical system represents a different candidate impedance sensing vector. A set of sensing vectors is selected in advance (via device programming) from among the candidate vectors. Sensing vectors are preferably selected such that each includes at least one electrode mounted on or in the ventricular myocardium so that the impedance signals detected along those vectors are thereby strongly affected by ventricular contractions. That is, electrode pairs are selected such that contraction of the ventricular myocardium significantly changes the impedance between the electrode pairs so as to produce a strong time-varying impedance waveform representative of ventricular contraction.

In one particular example (described below with reference to FIG. 5), an RV ring electrode is used in combination with each of a set of five LV electrodes of a multipolar lead so as to defined a set of five sensing vectors: RVring—LVe1; RVring—LVe2; RVring—LVe3; RVring—LVe4, etc. However, other combinations of electrodes can be used to define sensing vectors—so long as the resulting impedance signals are affected by the mechanical contraction of the heart to thereby have a cardiogenic component. The use of electrodes mounted on or in the LV of the patient is preferred since the resulting signals will be strongly affected by mechanical contraction of the LV and relatively free of variations due to respiration or other factors.

Note also that, rather than detecting impedance, other related electrical signals can be exploited, such as admittance, resistance or conductance or their equivalents. Admittance is the numerical reciprocal of impedance. Conductance is the numerical reciprocal of resistance. In general, impedance and admittance are vector quantities, which may be represented by complex numbers (having real and imaginary components.) The real component of impedance is resistance. The real component of admittance is conductance. When exploiting only the real components of these values, conductance can be regarded as the reciprocal of impedance. Likewise, when exploiting only the real components, admittance can be regarded as the reciprocal of resistance. Immittance represents either impedance or admittance. For the sake of generality, the term "impedance" as used herein encompasses any of these equivalent electrical signal parameters. These may also be referred to as immittance-based parameters.

At step 204, the pacer/ICD then compares the cardiogenic impedance signals detected along the different vectors to identify differences in morphological parameters affected by mechanical dyssynchrony including one or more of: (1) peak magnitude delay times of the cardiogenic impedance signals; (2) peak velocity delay times of the cardiogenic impedance signals; (3) peak magnitudes of the cardiogenic impedance signals; and (4) integrals of the cardiogenic impedance signals.

FIG. 4 illustrates these parameters by way of an exemplary impedance signal or waveform 212 corresponding to the contraction of the heart along one particular segment of the heart (i.e. along once sensing vector between one pair of electrodes.) In the example, an A-pulse is applied to the atria at time 214, resulting in the electrical depolarization of the atria shortly thereafter. Atrial depolarization is manifest within the RA IEGM as a P-wave 216. The slight delay between delivery of the A-pulse and depolarization of the atria is due to the time required for the atrial myocardial fibers to begin to depolarize in response to the stimulus. Following an atrioventricular conduction time delay, the ventricles then electrically depolarize and contract. The depolarization of the ventricles is manifest in the IEGM as a QRS-complex, which is typically much larger than the P-wave. (For the sake of clarity in illustrating other signals of interest, the large QRS-complex is not shown in the figure.)

Depolarization of the ventricles causes the ventricles to contract, which in turn causes a change in the magnitude of an impedance signal measured between a pair of sensing electrodes having a sensing vector crossing the ventricles, resulting in time-varying impedance waveform 212. The impedance along the sensing vector changes as the myocardium contracts primarily because the amount of fluid (i.e. blood) between the electrodes along the vector decreases as the ventricles contract, thus decreasing the impedance between the electrodes. In other words, ventricular contraction causes a negative deflection in an impedance signal relative to a baseline. With the techniques described herein, the magnitude (i.e. the absolute value) of the impedance signal is used so that the polarity of the impedance signal (negative deflection vs. positive deflection) is not important.

In the particular example of FIG. 4, the magnitude of the impedance signal increases quickly as the ventricles contract, then decreases more slowly as the ventricles relax back to their original state. As the ventricular myocardium relaxes, the ventricles electrically repolarize. Repolarization of the ventricles is manifest within the IEGM as a T-wave. (For the sake of clarity in illustrating other signals of interest, the T-wave is not shown in the figure.)

To detect the peak magnitude delay time 218 of the cardiogenic impedance signal, the pacer/ICD first detects the peak magnitude 220 of the absolute value of the impedance waveform (relative to a baseline value 222), then determines the time interval from A-pulse delivery time 214 to the peak magnitude time 224. To detect the peak velocity delay time, the pacer/ICD determines the first time derivative of the cardiogenic impedance (CI) signal (i.e. dCI/dt), then detects the maximum value of the time derivative. This maximum value represents the maximum speed or velocity of the ventricular myocardium (along the sensing vector). In the example of FIG. 4, the maximum velocity occurs at time 226. The pacer/ICD then determines the time interval from A-pulse delivery time 214 to the peak velocity time 226, which is identified in the figure as delay interval 228.

For the peak magnitude of the impedance signal, the pacer/ICD merely uses the peak magnitude value already determined (during detection of the peak magnitude time delay.) In FIG. 4, this peak magnitude value is specifically shown by way of arrow 230. To detect the integral 232 of the cardiogenic impedance signal, the pacer/ICD sums or integrates the area under the impedance waveform using otherwise conventional numerical integration techniques.

The morphological parameters are detected along each of the selected set of sensing vectors. Hence, if there are five sensing vectors, the pacer/ICD will determined five separate values for each of the parameters, i.e. five separate values for peak magnitude time delay, peak velocity time delay, etc. (Preferably, each of the various morphological parameters detected by the pacer/ICD along a given impedance sensing vector are ensemble averaged over a set of heartbeats before the morphological parameters are calculated. This will be discussed further below.)

Returning to FIG. 3, the parameters detected within step 204 for the separate sensing vectors are compared against one another to detect differences, if any. For the example where there are five sensing vectors, the pacer/ICD numerically quantifies the differences between the five separate values for peak magnitude time delay, then separately quantifies the differences between the five separate values for peak velocity time delay, etc. Any of a variety of otherwise conventional numerical comparison techniques can be used to quantify the differences among these values such as by, e.g., calculating standard deviation values. In general, the greater the differences among the values derived from the different sensing vectors, the greater the degree of mechanical dyssynchrony.

At step 206 of FIG. 3, the pacer/ICD, then detects akinetic segments, hypokinetic segments and late contracting segments based on the differences in the morphological parameters of the cardiogenic signal.

FIG. 5 illustrates exemplary hypokinetic segments and late contracting segments, along with cut-away views of the heart of a patient illustrating five sensing vectors. In particular, the figure illustrates a heart 250 with an RV lead 252 (having at least an RV ring electrode) and an LV lead 254 (also called a coronary sinus lead, see below) with a set of LV electrodes. Five cardiogenic impedance sensing vectors 256 are provided between the RV ring electrode and the LV electrodes and are identified herein as CI(E1)-CI(E5).

The figure further illustrates mechanically synchronous LV activation by way of heart illustration 250' and mechanically dyssynchronous LV activation by way of heart illustration 250". In this example, during synchronous activation, the electrodes of lead 254 are substantially uniformly displaced during contraction to a contracted position 258. As such, each of the impedance waveforms measured along the different sensing vectors changes at about the same time and by about the same amount. This is illustrated by way of impedance waveform graphs 260, each exhibiting similar time delays, magnitudes and waveform shapes. As such, each likewise has similar values for peak magnitude delay time, peak velocity delay time, peak magnitude, and waveform integral.

However, during dyssynchronous activation, the electrodes of lead 254 are not uniformly displaced during contraction, yielding a non-uniform contracted position 262. As such, each of the impedance waveforms measured along the different sensing vectors changes at somewhat different times and by somewhat different amounts. This is illustrated by way of impedance waveform graphs 264, which no longer exhibit the same time delays, magnitudes and waveform shapes for each vector. In this particular example, the portion or segment of the ventricular myocardium through which sensing vector CI(E2) passes contracts after the other segments have contracted, i.e. it is a late contracting segment. As a result, the impedance waveform sensed along the corresponding vector is delayed relative to the other impedance waveforms, as shown by way of waveform 266. Accordingly, the late contracting segment will have a different value for the peak magnitude delay time and the peak velocity delay time as compared to the other impedance signals. In the example, that particular segment of the myocardium also contracts by a smaller amount (i.e. it is hypokinetic), resulting in a smaller waveform, as also shown by way of waveform 266. Accordingly, the impedance waveform sensed along the corresponding vector has a smaller peak magnitude and a smaller integral value.

Although not shown in the example of FIG. 5, in some patients, some segments of the ventricular myocardium might not contract at all, resulting in little or no change in impedance along the corresponding sensing vector, i.e. the segment is akinetic. Accordingly, the impedance waveform sensed along that vector will be substantially flat. The peak magnitude (measured relative to baseline) and the signal integral will therefore both be near zero.

Hence, FIG. 5 illustrates an example wherein healthy synchronous contraction of the LV myocardium results in impedance waveforms having substantially similar time delays (relative to the A-pulse) and also having substantially similar peak magnitudes and signal integral values. As can be appreciated, even within a healthy heart, there is typically some variation in these values from vector to vector. Accordingly, only significant deviations among these values are deemed to be indicative of mechanical dyssynchrony. Also, with regard to peak magnitude values and signal integral values, even within a healthy heart there can be variations in these values from one sensing vector to another due to the relative orientations of the sensing vectors. In particular, a sensing vector utilizing an LV electrode near the apex of the ventricles might exhibit a smaller deflection in the impedance signal during contraction than a sensing vector utilizing an LV electrode further from the apex of the ventricles. In the example of FIG. 5, sensing vector 270 may exhibit less of a change in impedance during contraction than sensing vector 272, even though the LV is contracting synchronously. Hence, the measured values of peak magnitude and signal integral are preferably normalized. For example, following device implant, nominal values for peak magnitude and waveform signal integral along each sensing vector are measured, then normalized. Thereafter, only variations from those normalized values are used to detect hypokinetic segments.

Normalization is not required for the aforementioned time delay values. Within a healthy heart, these time delay values (measured relative to the time of delivery of the A-pulse) are substantially similar from one vector to another even though the various LV electrodes of the different vectors are positioned at different locations and at different distances from the atria. That is, within a healthy heart, all segments of the ventricular myocardium contract at substantially the same time regardless of their relative location within the LV. Note, though, that the actual duration of the interval from A-pulse to LV contraction will depend on patient heart rate and other factors. Accordingly, a uniform increase or decrease in the time delay values measured along all of the vectors is not indicative of mechanical dyssynchrony. Rather, it is the variation (if any) in time delay values from one vector to another that is instead indicative of dyssynchrony.

Figure 6:
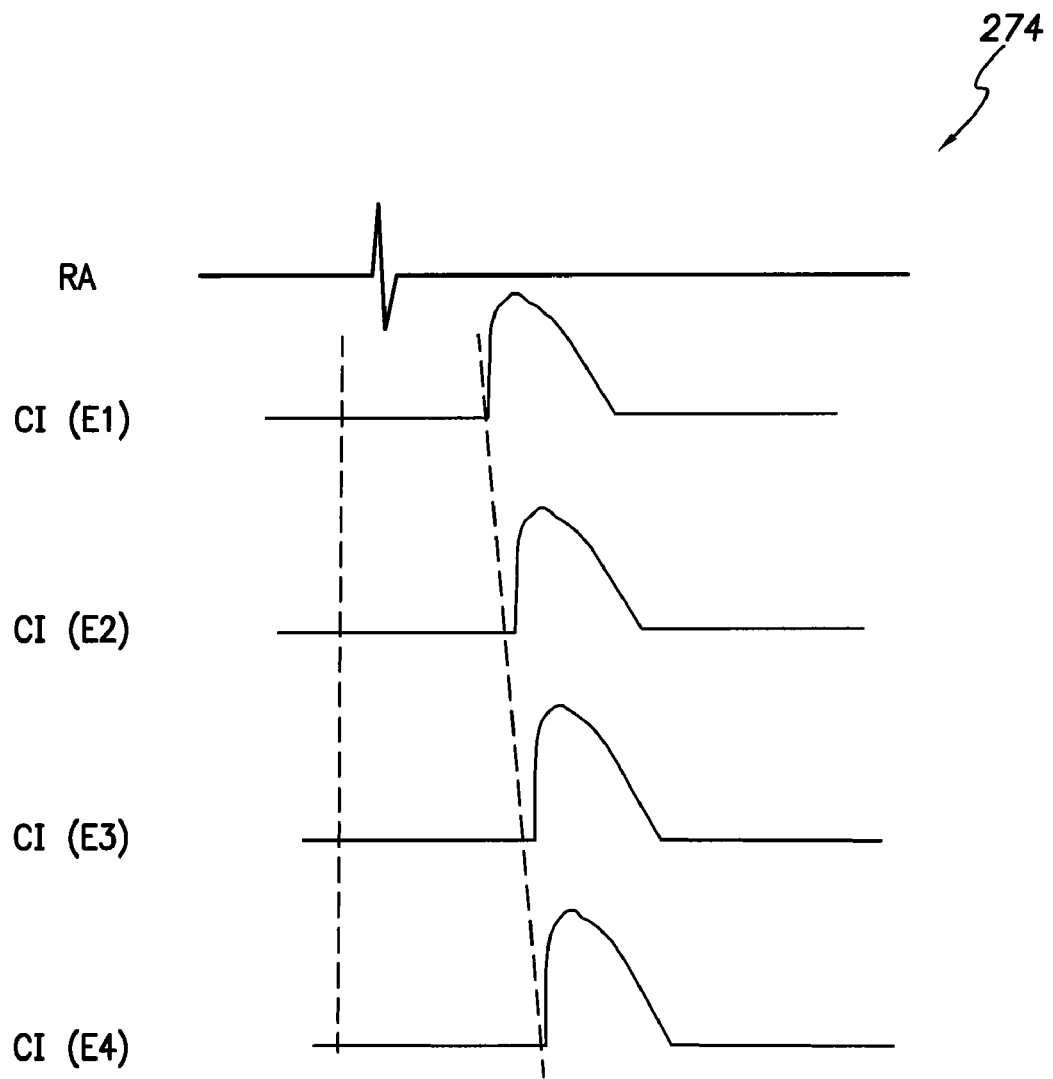
FIG. 6 is a graph illustrating a conduction defect resulting in the sequential mechanical contraction of segments of the heart, which may be detected using the technique of FIG. 3.

Note also that, within some unhealthy hearts, conduction defects can cause segments of the LV to contract sequentially, rather than simultaneously. This is illustrated by way of the graphs of FIG. 6. That is, within FIG. 6, a set of cardiogenic impedance waveforms 274 are illustrated wherein there is a sequentially variation in contraction times, indicative of possible conduction defects within the heart of the patient. This is yet another form of dyssynchrony that the pacer/ICD can detect using the techniques of the invention.

Returning to FIG. 3, at step 208, the pacer/ICD then generates a measure of global mechanical synchrony of the heart of the patient based on the differences (if any) in the cardiogenic signals. For example, using otherwise standard numerical techniques, the pacer/ICD can generate or calculate a single numerical value (e.g. a metric) indicative of the total amount of variation among the various morphological parameters of the cardiogenic impedance signal. At step 210, the pacer/ICD assesses the global hemodynamics of the heart of the patient based on the measure of global mechanical synchrony. The greater the value of the metric, the greater the amount of mechanical dyssynchrony, i.e. the poorer the overall state of global hemodynamics. For example, the metric may be compared against one or more threshold values indicative of global hemodynamics. The metric may be tracked over time to detect trends indicative of progression of heart failure. Warning signals can then be generated, therapy controlled, etc., as already explained. Diagnostic trend data can be stored.

The assessment of the hemodynamics of the heart can be performed in conjunction with other evaluation systems and techniques that also exploit impedance data, IEGM signals or other parameters detected within the patient. See, for example, techniques described in the aforementioned U.S. Pat. No. 7,676,264 of Pillai et al., as well as pending U.S. patent application Ser. No. 11/558,194, of Panescu et al., filed Nov. 9, 2006, entitled "Closed-Loop Adaptive Adjustment of Pacing Therapy based on Cardiogenic Impedance Signals Detected by an Implantable Medical Device"; pending U.S. patent application Ser. No. 11/557,887, of Shelchuk, filed Nov. 8, 2006, entitled "Systems and Methods for Evaluating Ventricular Dyssynchrony Using Atrial and Ventricular Pressure Measurements obtained by an Implantable Medical Device"; and U.S. Pat. No. 7,072,715 to Bradley, entitled "Implantable Cardiac Stimulation Device for and Method of Monitoring Progression or Regression of Heart Disease by Monitoring Evoked Response Features."

As noted, ventricular dyssynchrony may arise due to heart failure and hence any degradation in ventricular dyssynchrony might be indicative of progression of heart failure. Depending upon the capabilities of the pacer/ICD, heart failure may be corroborated by other suitable detection techniques. See, for example, U.S. Pat. No. 6,922,587, entitled "System and Method for Tracking Progression of Left Ventricular Dysfunction Using Implantable Cardiac Stimulation Device"; U.S. Pat. No. 6,942,622, entitled "Method For Monitoring Autonomic Tone"; U.S. Pat. No. 6,748,261, cited above, U.S. Pat. No. 6,741,885, entitled "Implantable Cardiac Device For Managing the Progression of Heart Disease and Method"; U.S. Pat. No. 6,643,548, entitled "Implantable Cardiac Stimulation Device for Monitoring Heart Sounds to Detect Progression and Regression of Heart Disease And Method Thereof"; U.S. Pat. No. 6,572,557, entitled "System And Method For Monitoring Progression Of Cardiac Disease State Using Physiologic Sensors"; U.S. Pat. No. 6,527,729, entitled "Method For Monitoring Patient Using Acoustic Sensor"; U.S. Pat. No. 6,512,953, entitled "System and Method for Automatically Verifying Capture During Multi-Chamber Stimulation" and U.S. Pat. No. 6,480,733, entitled "Method for Monitoring Heart Failure", each assigned to Pacesetter, Inc.

See, also, U.S. Pat. No. 7,272,443, filed Dec. 15, 2004, of Bornzin et al., entitled "System and Method for Predicting a Heart Condition Based on Impedance Values Using an Implantable Medical Device", and U.S. Pat. No. 7,094,207, filed Mar. 2, 2004, entitled "System and Method for Diagnosing and Tracking Congestive Heart Failure Based on the Periodicity of Cheyne-Stokes Respiration Using an Implantable Medical Device"; and U.S. Pat. No. 7,672,716 of Koh, entitled "QT-Based System and Method for Detecting and Distinguishing Dilated Cardiomyopathy and Heart Failure Using an Implantable Medical Device", also assigned to Pacesetter, Inc.

Figure 7:
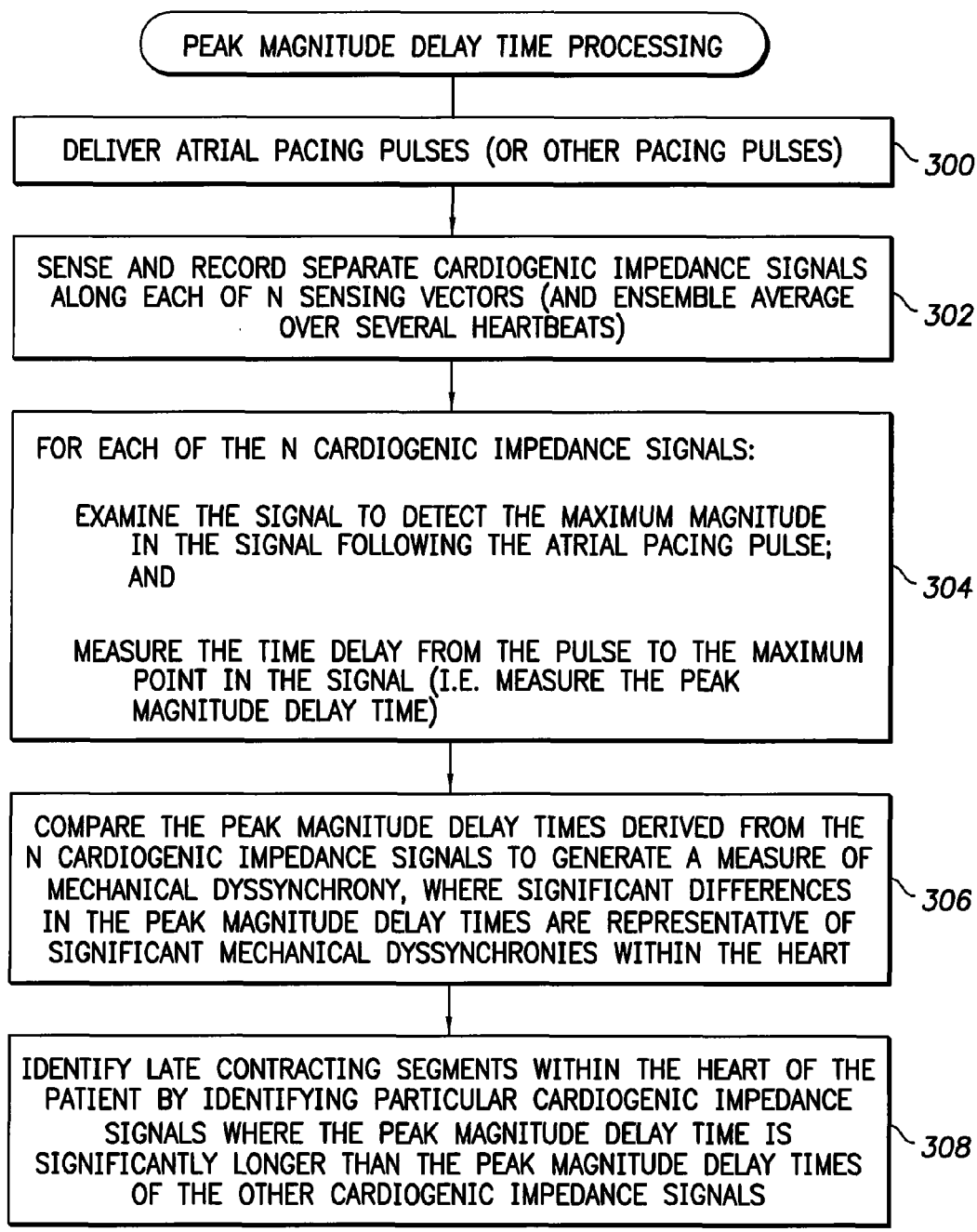
FIG. 7 specifically illustrates peak magnitude delay time processing, which may be performed in accordance with the exemplary technique of FIG. 3 to detect hypokinetic and late contracting segments.
Figure 8:
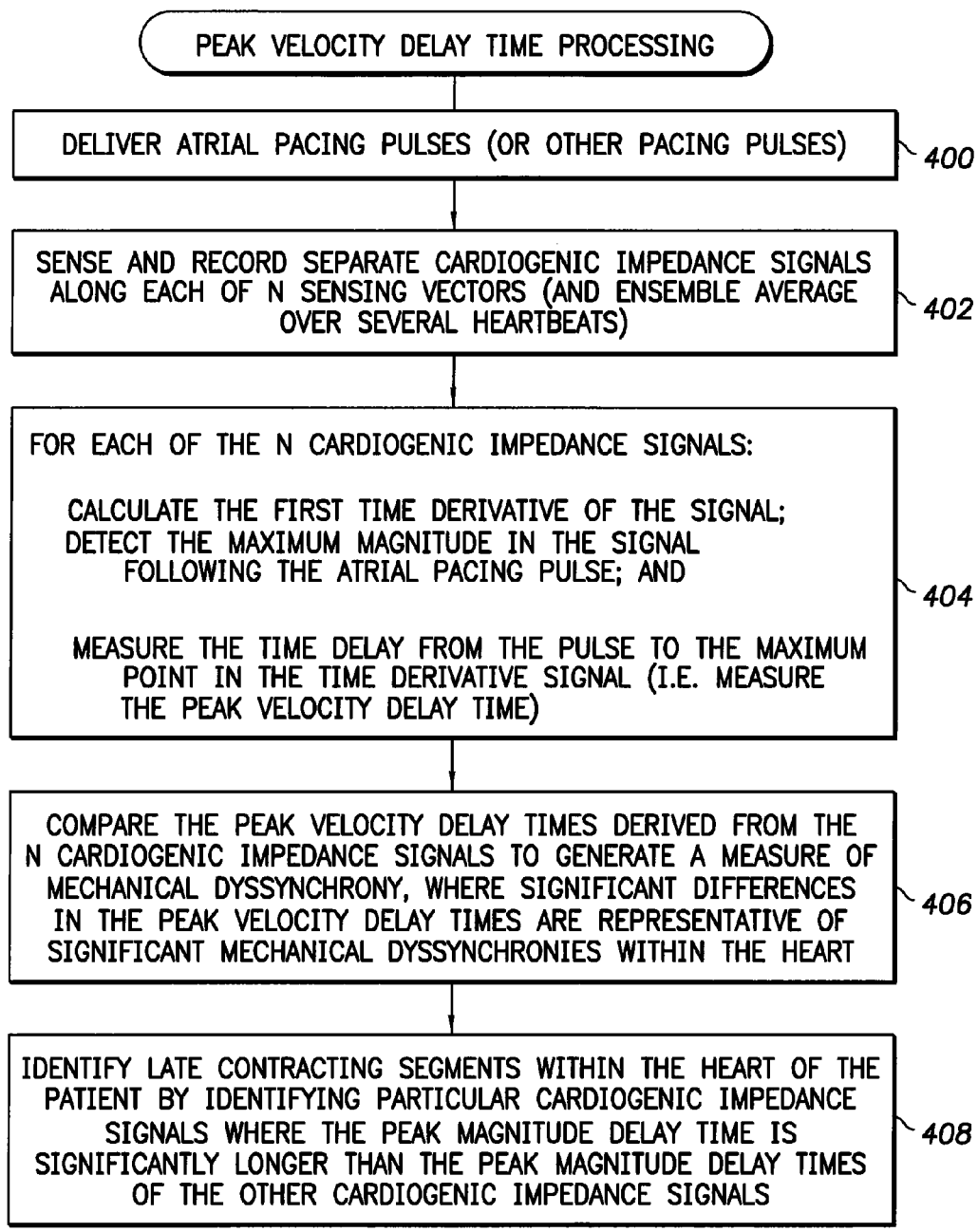
FIG. 8 specifically illustrates peak velocity delay time processing, which may be performed in accordance with the exemplary technique of FIG. 3 to detect late contracting segments.
Figure 9:
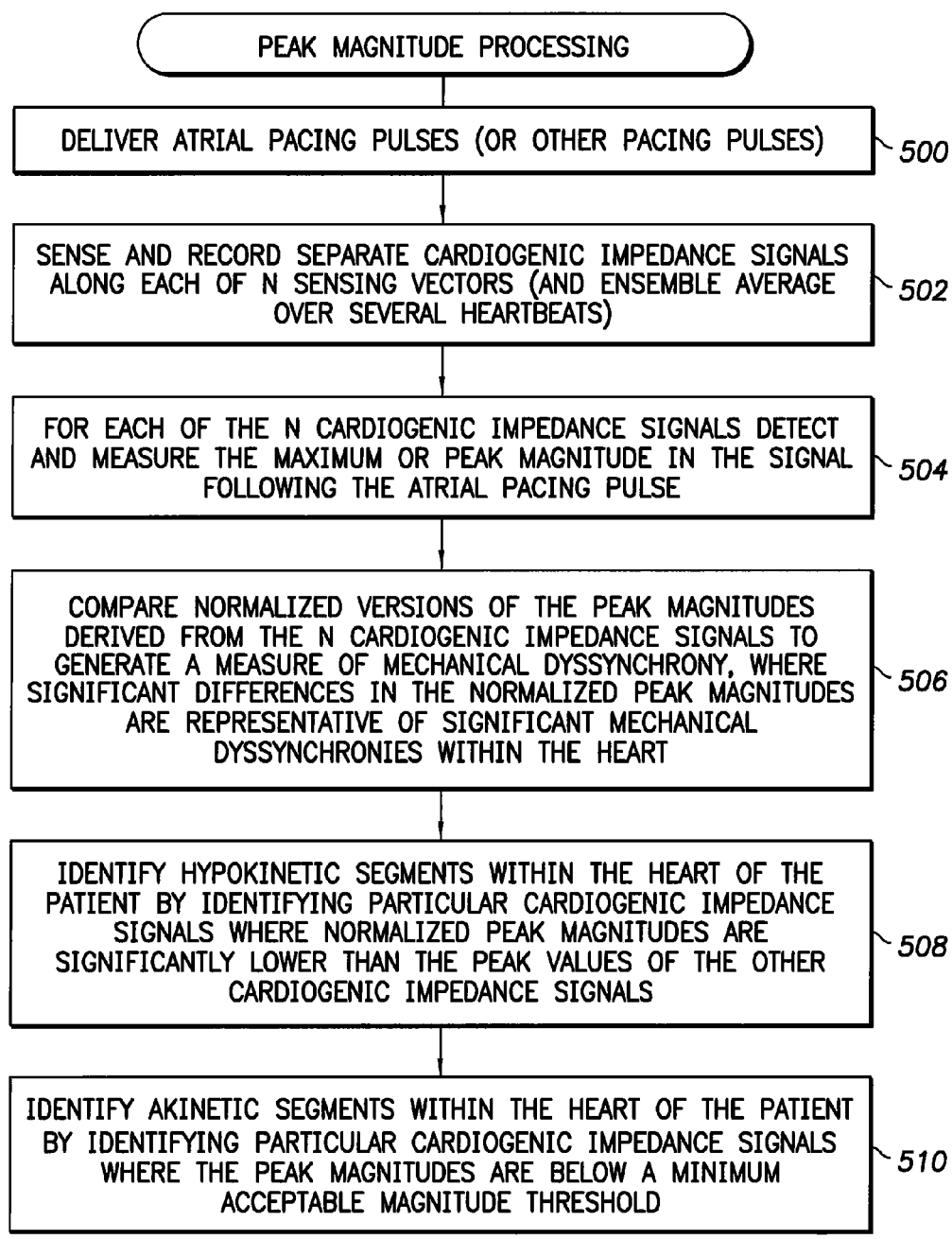
FIG. 9 specifically illustrates peak magnitude processing, which may be performed in accordance with the exemplary technique of FIG. 3 to detect hypokinetic and akinetic segments.

Turning now to FIGS. 7-9, further details regarding the processing of the aforementioned morphological parameters will now be provided.

FIG. 7 particularly illustrates peak magnitude delay time processing. Beginning at step 300, A-pulses (or other pacing pulses, such as RV-pulses) are delivered to the heart of the patient so as to provide a point of origin from which ventricular contraction delays can be measured. If the patient is already subject to therapeutic atrial pacing (e.g. to mitigate bradycardia), the pacer/ICD simply delivers A-pulses in accordance with that on-going therapy. If A-pulses are not already being delivered, the pacer/ICD can initiate a regime of atrial pacing specifically for the purposes of evaluating the mechanical synchrony of the heart. This may be performed periodically such, e.g., once per day. In any case, at step 302, the pacer/ICD senses and records separate cardiogenic impedance signals along each of N sensing vectors, such as the five vectors shown in FIG. 5. A greater number of sensing vectors provides for greater resolution. Preferably, the pacer/ICD senses and records impedance signal waveforms for each of a set of consecutive heartbeats (such as ten consecutive heartbeats), then ensemble averages the waveforms over the set of heartbeats to provide an averaged waveform for analysis.

At step 304, for each of the N cardiogenic impedance signals, the pacer/ICD then: examines the signal to detect the maximum magnitude in the signal following the atrial pacing pulse (or other pacing pulse used as a point of origin) and measures the time delay from the pulse to the maximum point in the absolute value of the signal. This time delay is recorded as the peak magnitude delay time. At step 306, the pacer/ICD then compares the peak magnitude delay times derived from each of the N cardiogenic impedance signals to generate a measure of mechanical dyssynchrony, where significant differences in peak magnitude delay times are representative of significant mechanical dyssynchronies within the heart.

At step 308, the pacer/ICD then identifies late contracting segments (if any) within the heart of the patient by identifying particular cardiogenic impedance signals from the set of N signals where the peak magnitude delay time is significantly longer than the peak magnitude delay times of the other cardiogenic impedance signals (as with waveform 266 of FIG. 5.) In this regard, the pacer/ICD may exploit a predetermined peak magnitude delay time threshold indicative of an abnormally long time delay. The threshold may be programmed in advance by the clinician or set to a default value. In one particular example, if the peak magnitude time delay for one particular vector is at least 10% longer than the time delays values of the other vectors, the time delay is deemed to be abnormally long, i.e. the segment is late contracting. Otherwise routine experimentation can be performed to identify optimal or preferred threshold values.

Diagnostic information identifying any late contracting segments may be recorded for clinician review. Also, as already explained, the amount of variation in the peak magnitude delay times can be incorporated into a metric representative of the global hemodynamics.

FIG. 8 illustrates peak velocity delay time processing. Many of the steps are the same or similar to those of FIG. 7 and those steps will only be briefly mentioned. At step 400, A-pulses (or other pacing pulses) are delivered and, at step 402, separate cardiogenic impedance signals are sensed and recorded for each of N sensing vectors. At step 404, for each of the N cardiogenic impedance signals, the pacer/ICD then: calculates the first time derivative of the signal; detects the maximum magnitude in the signal following the atrial pacing pulse (or other pacing pulse used as a point of origin); and measures the time delay from the pulse to the maximum point in the time derivative signal. This time delay is recorded as the peak velocity delay time.

At step 406, the pacer/ICD then compares the peak velocity delay times derived from each of the N cardiogenic impedance signals to generate a measure of mechanical dyssynchrony. At step 408, the pacer/ICD then identifies late contracting segments (if any) within the heart of the patient relative to a predetermined delay threshold. Diagnostic information identifying any late contracting segments is recorded for clinician review. Also, as already explained, the amount of variation in the peak velocity delay times can be incorporated into the metric representative of the global hemodynamics.

FIG. 9 illustrates peak magnitude processing. At step 500, A-pulses (or other pacing pulses) are delivered and, at step 502, cardiogenic impedance signals are sensed and recorded. At step 504, for each of N cardiogenic impedance signals, the pacer/ICD detects and measures the maximum or peak magnitude in the absolute value of signal following the atrial pacing pulse (or other pacing pulse used as a point of origin). At step 506, the pacer/ICD compares normalized versions of the peak magnitude values derived from the N cardiogenic impedance signals to generate a measure of mechanical dyssynchrony, where significant differences in the normalized peak magnitudes are representative of significant mechanical dyssynchronies within the heart.

At step 508, the pacer/ICD then identifies hypokinetic segments (if any) within the heart of the patient by identifying particular cardiogenic impedance signals where normalized peak magnitudes are significantly lower than the peak magnitude values of the other cardiogenic impedance signals (as with waveform 268 of FIG. 5.) The pacer/ICD may exploit a predetermined peak magnitude threshold indicative of an abnormally low peak magnitude. The threshold may be programmed in advance by the clinician or set to a default value. In one particular example, if the normalized peak magnitude for one particular vector is at least 10% lower than the normalized peak magnitudes of the other vectors, the segment is deemed to be hypokinetic. Otherwise routine experimentation can be performed to identify optimal or preferred threshold values.

At step 510, the pacer/ICD also identifies akinetic segments (if any) within the heart of the patient by identifying particular cardiogenic impedance signals where the peak magnitudes are below a minimum acceptable predetermined magnitude threshold. The threshold may be programmed in advance by the clinician or set to a default value. In one particular example, if the normalized peak magnitude for one particular vector is no greater than 5% of its initial normalized peak magnitude, the segment is deemed to be akinetic. Again, otherwise routine experimentation can be performed to identify optimal or preferred threshold values.

Figure 10:
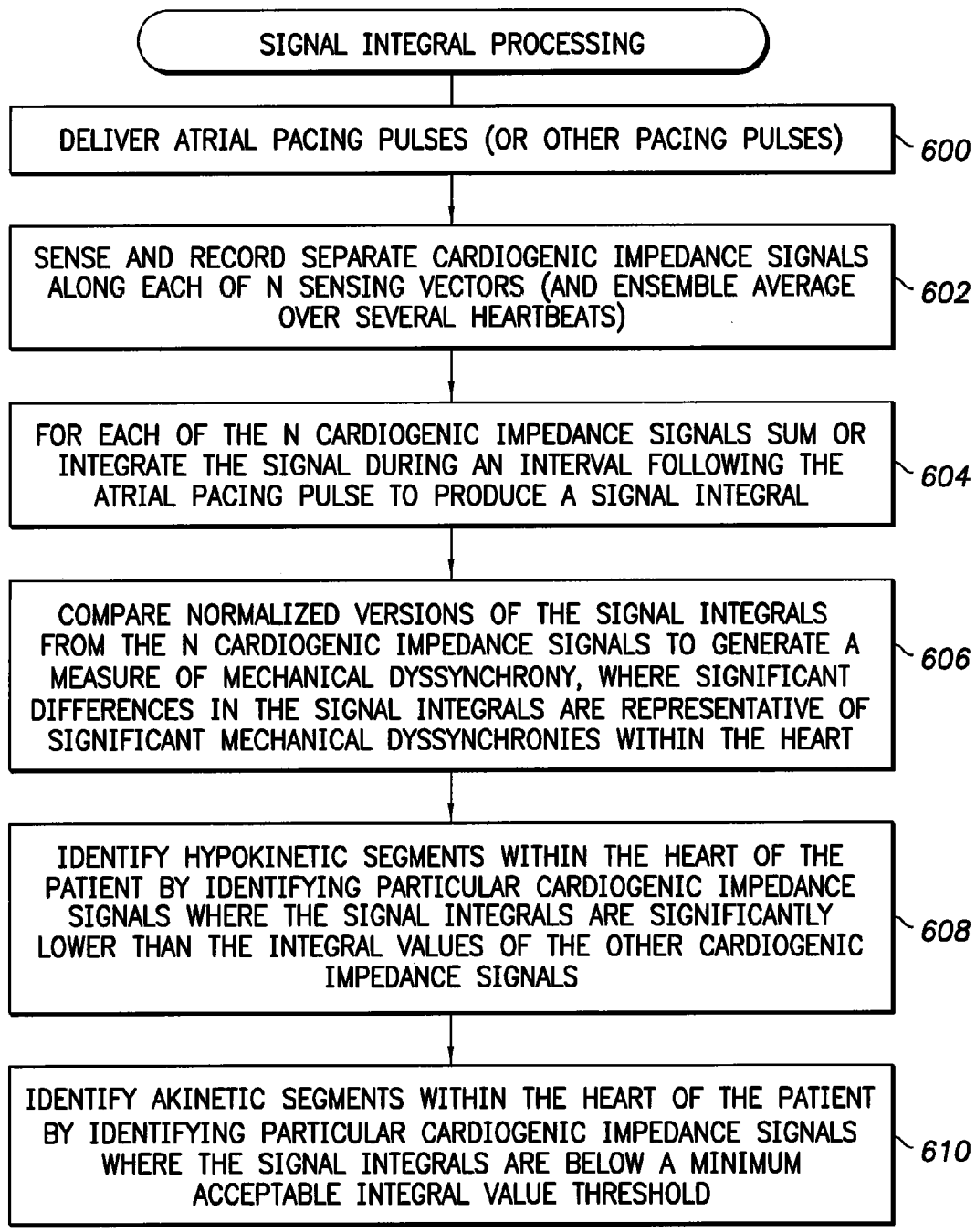
FIG. 10 specifically illustrates signal integral processing, which may be performed in accordance with the exemplary technique of FIG. 3 to detect hypokinetic and akinetic segments.

FIG. 10 illustrates signal integral processing. At step 600, A-pulses (or other pacing pulses) are delivered and, at step 602, cardiogenic impedance signals are sensed and recorded. At step 604, for each of N cardiogenic impedance signals, the pacer/ICD sums or integrates the waveform of the impedance signal following the atrial pacing pulse (or other pacing pulse used as a point of origin) to produce a signal or waveform integral. At step 606, the pacer/ICD then compares normalized versions of the signal integral values derived from the N cardiogenic impedance signals to generate a measure of mechanical dyssynchrony, where significant differences in the normalized signal integral are representative of significant mechanical dyssynchronies.

At step 608, the pacer/ICD then identifies hypokinetic segments (if any) within the heart of the patient by identifying particular cardiogenic impedance signals where normalized signal integral are significantly lower than the signal integral values of the other cardiogenic impedance signals. The pacer/ICD may exploit a predetermined signal integral threshold indicative of an abnormally signal integral. The threshold may be programmed in advance by the clinician or set to a default value. In one particular example, if the normalized signal integral for one particular vector is at least 10% lower than the normalized signal integral of the other vectors, the segment is deemed to be hypokinetic. Again, otherwise routine experimentation can be performed to identify optimal or preferred threshold values.

At step 610, the pacer/ICD also identifies akinetic segments (if any) within the heart of the patient by identifying particular cardiogenic impedance signals where the signal integral are below a minimum acceptable predetermined signal integral threshold. The threshold may be programmed in advance by the clinician or set to a default value. In one particular example, if the normalized signal integral for one particular vector is no greater than 5% of its initial normalized signal integral value, the segment is deemed to be akinetic. Again, otherwise routine experimentation can be performed to identify optimal or preferred threshold values.

What have been described are various techniques for evaluating cardiac mechanical dyssynchrony based on impedance parameters and for controlling therapy and other functions in response thereto. Although described primarily with reference to LV mechanical dyssynchrony, the techniques of the invention may also be applied, where appropriate, to detecting other forms of mechanical dyssynchrony, such as RV mechanical dyssynchrony, or even atrial mechanical dyssynchrony. Also, although particular morphological parameters are described herein (peak magnitude, etc.), these are merely exemplary and other suitable parameters derived from the cardiogenic impedance signals may be used, either additionally or alternatively.

For the sake of completeness, a detailed description of an exemplary pacer/ICD for evaluating cardiac mechanical dyssynchrony will now be provided. However, principles of invention may be implemented within other pacer/ICD implementations or within other implantable devices, including stand-alone mechanical dyssynchrony monitoring devices that do not provide pacing/sensing. Furthermore, although examples described herein involve processing of the various signals by the implanted device itself, some operations may be performed using an external device. For example, recorded impedance data may be transmitted to an external device, which processes the data to evaluate cardiac mechanical dyssynchrony. Processing by the implanted device itself is preferred as that allows prompt changes to pacing control parameters so as to address any progression in ventricular mechanical dyssynchrony.

Exemplary Pacemaker/ICD

FIG. 11 provides a simplified block diagram of the pacer/ICD, which is a multi-chamber stimulation device capable of treating both fast and slow arrhythmias with stimulation therapy, including cardioversion, defibrillation, and pacing stimulation, as well as being capable of performing the impedance-based functions discussed above. To provide atrial chamber pacing stimulation and sensing, pacer/ICD 10 is shown in electrical communication with a heart 712 by way of a left atrial lead 720 having an atrial tip electrode 722 and an atrial ring electrode 723 implanted in the atrial appendage. Pacer/ICD 10 is also in electrical communication with the heart by way of a right ventricular lead 730 having, in this embodiment, a ventricular tip electrode 732, a right ventricular ring electrode 734, a right ventricular (RV) coil electrode 736, and a superior vena cava (SVC) coil electrode 738. Typically, the right ventricular lead 718 is transvenously inserted into the heart to place the RV coil electrode 736 in the right ventricular apex, and the SVC coil electrode 738 in the superior vena cava. Accordingly, the right ventricular lead is capable of receiving cardiac signals, and delivering stimulation in the form of pacing and shock therapy to the right ventricle.

Figure 12:
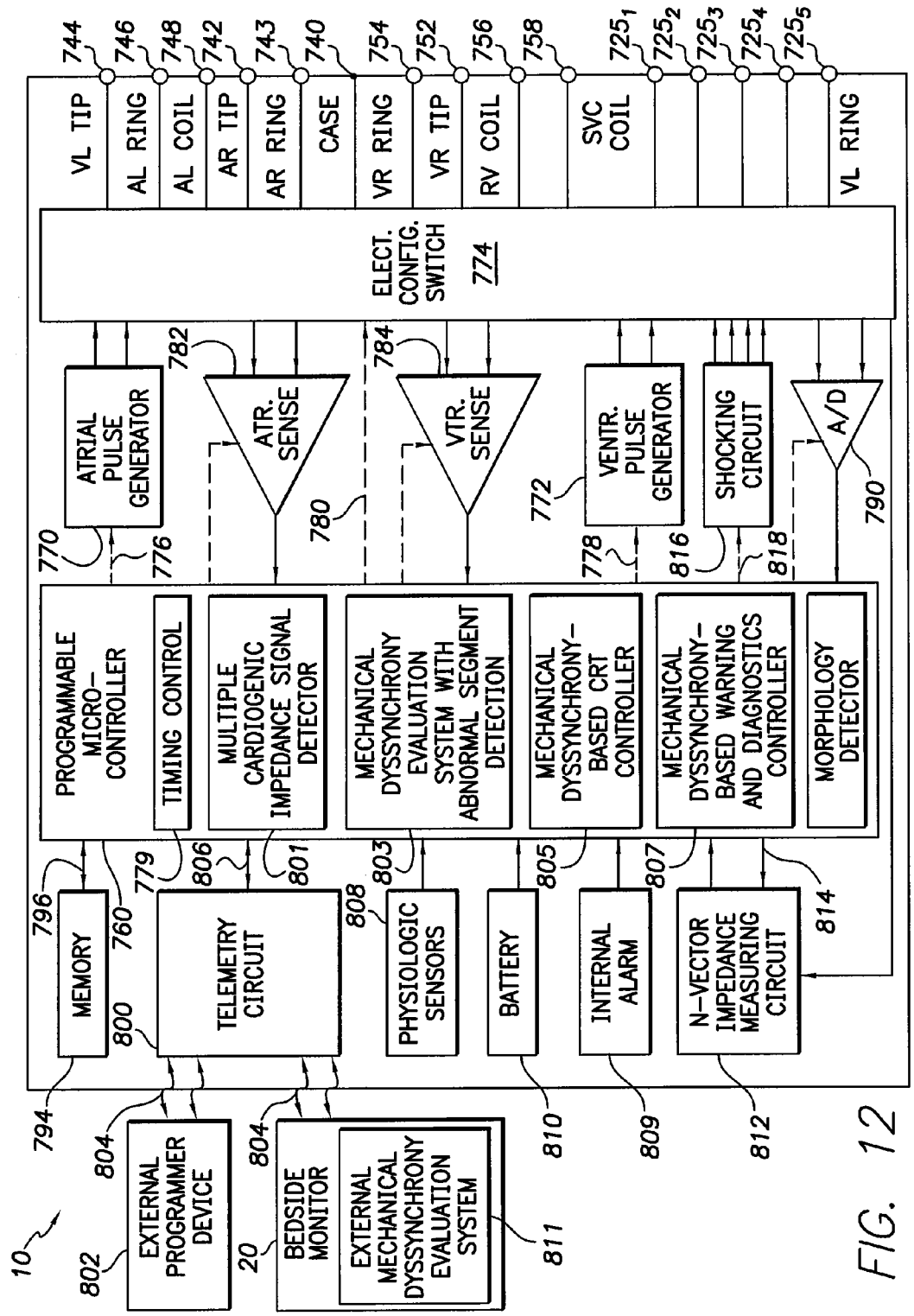
FIG. 12 is a functional block diagram of the pacer/ICD of FIG. 11, illustrating basic circuit elements that provide cardioversion, defibrillation and/or pacing stimulation in four chambers of the heart and particularly illustrating components for evaluating ventricular mechanical dyssynchrony based on cardiogenic impedance signals and for controlling therapy in response thereto.

To sense left atrial and ventricular cardiac signals and to provide left chamber pacing therapy, pacer/ICD 10 is coupled to a CS lead 724 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary CS lead 724 is designed to receive atrial and ventricular cardiac signals and to deliver left ventricular pacing therapy using at least a set of left ventricular ring electrodes $725_1$-$725_5$, a left ventricular tip electrode 726, and to deliver left atrial pacing therapy using at least a left atrial ring electrode 727, and shocking therapy using at least a left atrial coil electrode 728. With this configuration, biventricular pacing can be performed. Although only three leads are shown in FIG. 12, it should also be understood that additional stimulation leads (with one or more pacing, sensing and/or shocking electrodes) might be used in order to efficiently and effectively provide pacing stimulation to the left side of the heart or atrial cardioversion and/or defibrillation. Also, it should be understood that multiple ring electrodes may additionally or alternatively be provided on the RV lead or on the RA lead. Still more electrodes may be provide along the CS lead on or in the left atrium. In any case, a set of N sensing vectors is therapy provided for use in sensing separate cardiogenic impedance signals.

A simplified block diagram of internal components of pacer/ICD 10 is shown in FIG.12. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 740 for pacer/ICD 10, shown schematically in FIG. 12, is often referred to as the "can", "case" or "case electrode" and may be programmably selected to act as the return electrode for all "unipolar" modes. The housing 740 may further be used as a return electrode alone or in combination with one or more of the coil electrodes, 728, 736 and 738, for shocking purposes. The housing 740 further includes a connector (not shown) having a plurality of terminals, $725_1$-$725_5$, 742, 743, 744, 745 746, 748, 752, 754, 756 and 758 (shown schematically and, for convenience, the names of the electrodes to which they are connected are shown next to the terminals). As such, to achieve right atrial sensing and pacing, the connector includes at least a right atrial tip terminal ($A_R$ TIP) 742 adapted for connection to the atrial tip electrode 722 and a right atrial ring ($A_R$ RING) electrode 743 adapted for connection to right atrial ring electrode 723. To achieve left chamber sensing, pacing and shocking, the connector includes at least a left ventricular tip terminal ($V_L$ TIP) 744, a left atrial ring terminal ($A_L$ RING) 746, and a left atrial shocking terminal ($A_L$ COIL) 748, which are adapted for connection to the left ventricular tip electrode 726, the left atrial ring electrode 727, and the left atrial coil electrode 728, respectively. To support right chamber sensing, pacing and shocking, the connector further includes a right ventricular tip terminal ($V_R$ TIP) 752, a right ventricular ring terminal ($V_R$ RING) 754, a right ventricular shocking terminal ($V_R$ COIL) 756, and an SVC shocking terminal (SVC COIL) 758, which are adapted for connection to the right ventricular tip electrode 732, right ventricular ring electrode 734, the $V_R$ coil electrode 736, and the SVC coil electrode 738, respectively.

At the core of pacer/ICD 10 is microcontroller 760, which controls the various modes of stimulation therapy. As is well known in the art, the microcontroller 760 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 760 includes the ability to process or monitor input signals (data) as controlled by a program code stored in a designated block of memory. The details of the design and operation of the microcontroller 760 are not critical to the invention. Rather, any suitable microcontroller 760 may be used that carries out the functions described herein.

The use of microprocessor-based control circuits for performing timing and data analysis functions are well known in the art.

As shown in FIG. 12, an atrial pulse generator 770 and a ventricular pulse generator 772 generate pacing stimulation pulses for delivery by the right atrial lead 720, the right ventricular lead 730, and/or the CS lead 724 via an electrode configuration switch 774. It is understood that in order to provide stimulation therapy in each of the four chambers of the heart, the atrial and ventricular pulse generators, 770 and 772, may include dedicated, independent pulse generators, multiplexed pulse generators or shared pulse generators. The pulse generators, 770 and 772, are controlled by the microcontroller 760 via appropriate control signals, 776 and 778, respectively, to trigger or inhibit the stimulation pulses.

The microcontroller 760 further includes timing control circuitry 779 used to control the timing of such stimulation pulses (e.g., pacing rate, atrioventricular delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 774 includes a plurality of switches for connecting the desired electrodes to the appropriate I/O circuits, thereby providing complete electrode programmability. Accordingly, the switch 774, in response to a control signal 780 from the microcontroller 760, determines the polarity of the stimulation pulses (e.g., unipolar, bipolar, combipolar, etc.) by selectively closing the appropriate combination of switches (not shown) as is known in the art.

Atrial sensing circuits 782 and ventricular sensing circuits 784 may also be selectively coupled to the right atrial lead 720, CS lead 724, and the right ventricular lead 730, through the switch 774 for detecting the presence of cardiac activity in each of the four chambers of the heart. Accordingly, the atrial and ventricular sensing circuits, 782 and 784, may include dedicated sense amplifiers, multiplexed amplifiers or shared amplifiers. The switch 774 determines the "sensing polarity" of the cardiac signal by selectively closing the appropriate switches, as is also known in the art. In this way, the clinician may program the sensing polarity independent of the stimulation polarity. Each sensing circuit, 782 and 784, preferably employs one or more low power, precision amplifiers with programmable gain and/or automatic gain control and/or automatic sensitivity control, bandpass filtering, and a threshold detection circuit, as known in the art, to selectively sense the cardiac signal of interest. The automatic gain control and/or automatic sensitivity control enables pacer/ICD 10 to deal effectively with the difficult problem of sensing the low amplitude signal characteristics of atrial or ventricular fibrillation. The outputs of the atrial and ventricular sense amplifiers may be in the form of interrupts. The microcontroller 760 triggers or inhibits the atrial and ventricular pulse generators, 770 and 772, respectively, in a demand fashion in response to the absence or presence of cardiac activity in the appropriate chambers of the heart, as represented by the atrial and ventricular event interrupts.

For arrhythmia detection, pacer/ICD 10 utilizes the atrial and ventricular sensing circuits, 782 and 784, to sense cardiac signals to determine whether a rhythm is physiologic or pathologic. As used in this section "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 760 by comparing them to a predefined rate zone limit (i.e., bradycardia, normal, atrial tachycardia, atrial fibrillation, low rate ventricular tachycardia, high rate ventricular tachycardia, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 790. The data acquisition system 790 is configured to acquire intracardiac electrogram signals, convert the raw analog data into a digital signal, and store the digital signals for later processing and/or telemetric transmission to an external device 802. The data acquisition system 790 is coupled to the right atrial lead 720, the CS lead 724, and the right ventricular lead 718 through the switch 774 to sample cardiac signals across any pair of desired electrodes. The microcontroller 760 is further coupled to a memory 794 by a suitable data/address bus 796, wherein the programmable operating parameters used by the microcontroller 760 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 794 through a telemetry circuit 800 in telemetric communication with the external device 802, such as a programmer, transtelephonic transceiver or a diagnostic system analyzer. The telemetry circuit 800 is activated by the microcontroller by a control signal 806. The telemetry circuit 800 advantageously allows intracardiac electrograms and status information relating to the operation of pacer/ICD 10 (as contained in the microcontroller 760 or memory 794) to be sent to the external device 802 through an established communication link 804. Pacer/ICD 10 further includes an accelerometer or other physiologic sensor 808, commonly referred to as a "rate-responsive" sensor because it is typically used to adjust pacing stimulation rate according to the exercise state of the patient. However, the physiological sensor 808 may further be used to detect changes in cardiac output, changes in the physiological condition of the heart, or diurnal changes in activity (e.g., detecting sleep and wake states) and to detect arousal from sleep. Accordingly, the microcontroller 760 responds by adjusting the various pacing parameters (such as rate, AV delay, V-V delay, etc.) at which the atrial and ventricular pulse generators, 770 and 772, generate stimulation pulses. While shown as being included within pacer/ICD 10, it is to be understood that the physiologic sensor 808 may also be external to pacer/ICD 10, yet still be implanted within or carried by the patient. A common type of rate responsive sensor is an activity sensor incorporating an accelerometer or a piezoelectric crystal, which is mounted within the housing 740 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 810, which provides operating power to all of the circuits shown in FIG. 12. The battery 810 may vary depending on the capabilities of pacer/ICD 10. If the system only provides low-voltage therapy, a lithium iodine or lithium copper fluoride cell may be utilized. For pacer/ICD 10, which employs shocking therapy, the battery 810 must be capable of operating at low current drains for long periods, and then be capable of providing high-current pulses (for capacitor charging) when the patient requires a shock pulse. The battery 810 should also have a predictable discharge characteristic so that elective replacement time can be detected. Accordingly, pacer/ICD 10 is preferably capable of high-voltage therapy and appropriate batteries.

As further shown in FIG. 12, pacer/ICD 10 is shown as having an N-vector impedance measuring circuit 812 which is enabled by the microcontroller 760 via a control signal 814. The impedance circuit is used to detect separate cardiogenic impedance signals along vectors between the RV ring electrode and the five LV ring electrodes, or between other pairs or combinations of electrodes. Impedance values may also be used for tracking respiration; for surveillance during the acute and chronic phases for proper lead positioning or dislodgement; for measuring respiration or minute ventilation; for measuring thoracic impedance for use in setting shock thresholds; for detecting when the device has been implanted; and for detecting the opening of heart valves, etc. The impedance measuring circuit 817 is advantageously coupled to the switch 74 so that any desired combination of electrodes may be used.

In the case where pacer/ICD 10 is intended to operate as an ICD, it detects the occurrence of an arrhythmia, and automatically applies an appropriate electrical shock therapy to the heart aimed at terminating the detected arrhythmia. To this end, the microcontroller 760 further controls a shocking circuit 816 by way of a control signal 818. The shocking circuit 816 generates shocking pulses of low (up to 0.5 joules), moderate (0.5-10 joules) or high energy (11 to 40 joules or more), as controlled by the microcontroller 760. Such shocking pulses are applied to the heart of the patient through at least two shocking electrodes, and as shown in this embodiment, selected from the left atrial coil electrode 728, the RV coil electrode 736, and/or the SVC coil electrode 738. The housing 740 may act as an active electrode in combination with the RV electrode 736, or as part of a split electrical vector using the SVC coil electrode 738 or the left atrial coil electrode 728 (i.e., using the RV electrode as a common electrode). Cardioversion shocks are generally considered to be of low to moderate energy level (so as to minimize pain felt by the patient), and/or synchronized with a VF event and/or pertaining to the treatment of tachycardia. Defibrillation shocks are generally of moderate to high energy level (i.e., corresponding to thresholds in the range of 8-40 joules), delivered asynchronously (since VF events may be too disorganized), and pertaining exclusively to the treatment of fibrillation. Accordingly, the microcontroller 760 is capable of controlling the synchronous or asynchronous delivery of the shocking pulses.

Microcontroller 760 also includes various components for controlling or performing the various operations described above with reference to FIGS. 1-10. In particular, the microcontroller includes a multiple cardiogenic impedance signal detector 801 operative to detect a plurality of cardiogenic impedance signals along different sensing vectors within the patient, and a mechanical dyssynchrony evaluation system 803 operative to detect a measure of mechanical dyssynchrony in the heart of the patient based on the cardiogenic impedance signals, including detecting abnormally contracting segments, if any, within the heart of the patient. A mechanical dyssynchrony-based CRT controller 805 is operative to control CRT based, at least in part, in the measure of mechanical dyssynchrony to improve cardiac function. The microcontroller also includes a mechanical dyssynchrony-based warning and diagnostic controller 807 operative to control the generation of warning signals and to control recording of diagnostic information within memory 794 pertinent to mechanical dyssynchrony. Warnings may be issued via internal implanted alarm 809 or via bedside monitor 20.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

When used in conjunction with an external system such as a bedside monitor, the external system can perform some of the mechanical dyssynchrony evaluation functions, such as by analyzing impedance data transmitted from the pacer/ICD. This is shown by way of external mechanical dyssynchrony evaluation system 811 of the bedside monitor. In other words, not all of the functions need be performed by the pacer/ICD but functions can be distributed among various systems, some implanted within the patient, others external.

While the invention has been described with reference to particular exemplary embodiments, modifications can be made thereto without departing from scope of the invention. Note also that the term "including" as used herein is intended to be inclusive, i.e. "including but not limited to."

What is claimed is:

1. A method for use with an implantable medical device for implant within a patient, the method comprising:
   detecting a plurality of cardiogenic impedance signals along different sensing vectors within the patient;
   detecting a measure of mechanical dyssynchrony in the heart of the patient based on a comparison of the cardiogenic impedance signals, including detecting abnormally contracting segments, if any, within the heart of the patient; and
   controlling at least one device function based on the measure of mechanical dyssynchrony;
   wherein detecting the measure of mechanical dyssynchrony includes
      delivering a pacing pulse to the heart of the patient;
      for each of the cardiogenic impedance signals, examining the signal to detect a maximum in a first time derivative of the signal after pulse delivery and then measuring the time delay from the pulse to the maximum in the first time derivative; and comparing the peak velocity delay times derived from the cardiogenic impedance signals to generate the measure of mechanical dyssynchrony.

2. The method of claim 1 wherein detecting the plurality of cardiogenic impedance signals includes detecting individual cardiac impedance signals by:
   measuring a raw impedance signal along a selected sensing vector passing through the heart of the patient; and
   extracting a cardiogenic impedance signal (CI) from the raw impedance signal, wherein the cardiogenic impedance (CI) signal is representative of variations in impedance due to the beating of the heart of the patient.

3. The method of claim 1 wherein significant differences in the peak velocity delay times are representative of significant mechanical dyssynchronies within the heart.

4. The method of claim 1 wherein detecting abnormally contracting segments includes detecting one or more of akinetic segments, hypokinetic segments and late contracting segments.

5. The method of claim 1 wherein controlling at least one device function based on the measure of mechanical dyssynchrony includes one or more of: recording diagnostic information, generating warning signals, and controlling delivery of therapy.

6. The method of claim 1 wherein the steps are all performed by the implantable medical device.

7. The method of claim 1 wherein some of the steps are performed by the implantable medical device and others are performed by an external system.

8. A method for use with an implantable medical device for implant within a patient, the method comprising:
   detecting a plurality of cardiogenic impedance signals along different sensing vectors within the patient;
   detecting a measure of mechanical dyssynchrony in the heart of the patient based on a comparison of the cardiogenic impedance signals, including detecting abnormally contracting segments, if any, within the heart of the patient; and
   controlling at least one device function based on the measure of mechanical dyssynchrony;
   wherein detecting the measure of mechanical dyssynchrony includes detecting differences in peak velocity delay times observed within the cardiogenic impedance signals and identifying late contracting segments within the heart of the patient by identifying particular cardiogenic impedance signals wherein the peak velocity delay time is significantly longer than the peak velocity delay times of the other cardiogenic impedance signals.

9. A method for use with an implantable medical device for implant within a patient, the method comprising:
   detecting a plurality of cardiogenic impedance signals along different sensing vectors within the patient;
   detecting a measure of mechanical dyssynchrony in the heart of the patient based on a comparison of the cardiogenic impedance signals, including detecting abnormally contracting segments, if any, within the heart of the patient; and
   controlling at least one device function based on the measure of mechanical dyssynchrony;
   wherein detecting the measure of mechanical dyssynchrony includes detecting differences in integrals derived from the cardiogenic impedance signals.

10. The method of claim 9 wherein detecting differences in the cardiogenic impedance signal integrals includes:
    delivering a pacing pulse to the heart of the patient;
    for each of the cardiogenic impedance signals, integrated a portion of the signal detected after pulse delivery; and
    comparing the integrals derived from the cardiogenic impedance signals to generate the measure of mechanical dyssynchrony.

11. The method of claim 9 wherein significant differences in the cardiogenic impedance signal integrals are representative of significant mechanical dyssynchronies within the heart.

12. The method of claim 9 further including identifying hypokinetic segments within the heart of the patient by identifying cardiogenic impedance signals with integrals significantly smaller than the integrals of the other cardiogenic impedance signals.

13. The method of claim 9 further including identifying akinetic segments within the heart of the patient by identifying cardiogenic impedance signals with integrals below a minimum acceptable integral threshold.

14. The method of claim 9 wherein detecting the plurality of cardiogenic impedance signals includes detecting individual cardiac impedance signals by:
    measuring a raw impedance signal along a selected sensing vector passing through the heart of the patient; and
    extracting a cardiogenic impedance signal (CI) from the raw impedance signal, wherein the cardiogenic impedance (CI) signal is representative of variations in impedance due to the beating of the heart of the patient.

15. The method of claim 9 wherein detecting abnormally contracting segments includes detecting one or more of akinetic segments, hypokinetic segments and late contracting segments.

16. The method of claim 9 wherein controlling at least one device function based on the measure of mechanical dyssynchrony includes one or more of:
    recording diagnostic information, generating warning signals, and controlling delivery of therapy.

17. The method of claim 9 wherein the steps are all performed by the implantable medical device.

18. The method of claim 9 wherein some of the steps are performed by the implantable medical device and others are performed by an external system.

19. A system for use with an implantable medical device for implant within a patient, the system comprising:
    a multiple cardiogenic impedance signal detector operative to detect a plurality of cardiogenic impedance signals along different sensing vectors within the patient; and
    a mechanical dyssynchrony evaluation system operative to detect a measure of mechanical dyssynchrony in the heart of the patient based on a comparison of the cardiogenic impedance signals, including detecting abnormally contracting segments, if any, within the heart of the patient;
    wherein to detect the measure of mechanical dyssynchrony the mechanical dyssynchrony evaluation system is operative to deliver a pacing pulse to the heart of the patient; for each of the cardiogenic impedance signals, examine the signal to detect a maximum in a first time derivative of the signal after pulse delivery and then measure the time delay from the pulse to the maximum in the first time derivative; and compare the peak velocity delay times derived from the cardiogenic impedance signals to generate the measure of mechanical dyssynchrony.

20. The system of claim 19 further comprising:
    a controller operative to control at least one device function based on the measure of mechanical dyssynchrony.

21. The system of claim 20 wherein the controller includes a mechanical dyssynchrony-based cardiac resynchronization therapy (CRT) controller operative to control CRT based, at least in part, on the measure of mechanical dyssynchrony.

22. The system of claim 20 wherein the controller includes a mechanical dyssynchrony-based warning controller operative to control the generation of warning signals in response to an increase in mechanical dyssynchrony.

23. A method for use with an implantable medical device for implant within a patient, the method comprising:
  detecting a plurality of cardiogenic impedance signals along different sensing vectors within the patient;
  detecting a measure of mechanical dyssynchrony in the heart of the patient based on a comparison of the cardiogenic impedance signals, including detecting differences in integrals of the cardiogenic impedance signals; and
  controlling at least one device function based on the measure of mechanical dyssynchrony.

24. A system for use with an implantable medical device for implant within a patient, the system comprising:
  a multiple cardiogenic impedance signal detector operative to detect a plurality of cardiogenic impedance signals along different sensing vectors within the patient; and
  a mechanical dyssynchrony evaluation system operative to detect a measure of mechanical dyssynchrony in the heart of the patient based on a comparison of the cardiogenic impedance signals, including detecting abnormally contracting segments, if any, within the heart of the patient;
  wherein to detect the measure of mechanical dyssynchrony the mechanical dyssynchrony evaluation system is operative to detect differences in integrals derived from the cardiogenic impedance signals.

25. The system of claim 24 further comprising:
  a controller operative to control at least one device function based on the measure of mechanical dyssynchrony.

26. The system of claim 25 wherein the controller includes a mechanical dyssynchrony-based cardiac resynchronization therapy (CRT) controller operative to control CRT based, at least in part, on the measure of mechanical dyssynchrony.

27. The system of claim 25 wherein the controller includes a mechanical dyssynchrony-based warning controller operative to control the generation of warning signals in response to an increase in mechanical dyssynchrony.

* * * * *